US012268714B2

(12) United States Patent
Suganuma et al.

(10) Patent No.: US 12,268,714 B2
(45) Date of Patent: Apr. 8, 2025

(54) TRANSPLANTATION OF MITOCHONDRIA INTO LYMPHOID ORGAN AND COMPOSITION THEREFOR

(71) Applicant: LUCA Science Inc., Chuo-ku (JP)

(72) Inventors: Masashi Suganuma, Aichi (JP); Hideyoshi Harashima, Hokkaido (JP); Yuma Yamada, Hokkaido (JP); Daisuke Sasaki, Hokkaido (JP); Takafumi Yokota, Osaka (JP)

(73) Assignee: LUCA Science Inc., Chuo-ku (JP)

( * ) Notice: Subject to any disclaimer, the term of this patent is extended or adjusted under 35 U.S.C. 154(b) by 962 days.

(21) Appl. No.: 17/275,983

(22) PCT Filed: Sep. 13, 2019

(86) PCT No.: PCT/JP2019/036011
§ 371 (c)(1),
(2) Date: Mar. 12, 2021

(87) PCT Pub. No.: WO2020/054829
PCT Pub. Date: Mar. 19, 2020

(65) Prior Publication Data
US 2022/0031743 A1 Feb. 3, 2022

Related U.S. Application Data

(60) Provisional application No. 62/824,668, filed on Mar. 27, 2019, provisional application No. 62/731,731, filed on Sep. 14, 2018.

(51) Int. Cl.
*A61K 35/15* (2015.01)
*A61K 35/17* (2015.01)
*A61K 35/34* (2015.01)

(52) U.S. Cl.
CPC .............. *A61K 35/15* (2013.01); *A61K 35/17* (2013.01); *A61K 35/34* (2013.01)

(58) Field of Classification Search
None
See application file for complete search history.

(56) References Cited

U.S. PATENT DOCUMENTS

| | | |
|---|---|---|
| 2001/0021526 A1 | 9/2001 | Davis et al. |
| 2004/0166103 A1 | 8/2004 | Ikehara et al. |
| 2006/0161996 A1 | 7/2006 | Ishikawa et al. |
| 2006/0212954 A1 | 9/2006 | Prolla et al. |
| 2011/0008310 A1 | 1/2011 | Cataldo et al. |
| 2012/0308585 A1 | 12/2012 | Lombardo et al. |
| 2013/0236458 A1 | 9/2013 | Hsieh et al. |
| 2015/0018294 A1 | 1/2015 | DeBenedetti et al. |
| 2015/0313930 A1 | 11/2015 | Sinclair et al. |
| 2017/0049851 A1 | 2/2017 | Postrel |
| 2017/0065635 A1 | 3/2017 | Cataldo et al. |
| 2017/0066843 A1 | 3/2017 | Ulitin et al. |
| 2017/0290763 A1 | 10/2017 | Su et al. |
| 2018/0030413 A1 | 2/2018 | Yivgi-Ohana et al. |
| 2018/0042983 A1 | 2/2018 | Wilson |
| 2018/0057610 A1* | 3/2018 | McCully ................... A61P 1/18 |
| 2018/0071337 A1 | 3/2018 | Cataldo et al. |
| 2018/0085407 A1* | 3/2018 | Stolen .................. C12N 5/0696 |
| 2020/0032214 A1 | 1/2020 | Harashima et al. |
| 2020/0316115 A1 | 10/2020 | Cataldo et al. |

FOREIGN PATENT DOCUMENTS

| | | |
|---|---|---|
| CN | 1835679 A | 9/2006 |
| CN | 105854030 A | 8/2016 |
| JP | 2003-533219 A | 11/2003 |
| JP | 2004-256444 A | 9/2004 |
| JP | 2004-339227 A | 12/2004 |
| JP | 2012-532859 A | 12/2012 |
| JP | 2017-55729 A | 3/2017 |
| JP | 2017-530148 A | 10/2017 |
| JP | 2018-35149 A | 3/2018 |
| JP | 2018-507690 A | 3/2018 |
| WO | WO 95/13697 A1 | 5/1995 |
| WO | WO 01/87982 A2 | 11/2001 |
| WO | WO 03/070083 A2 | 8/2002 |
| WO | WO2007020244 A1 | 2/2007 |
| WO | WO 2008/137035 A1 | 11/2008 |

(Continued)

OTHER PUBLICATIONS

Griffith et al. Metabolic damage and premature thymus aging caused by stromal catalase deficiency. Cell Reports 2015, 12:1071-1079. (Year: 2015).*
Moreadith et al. Isolation of mitochondria from ascites tumor cells permeabilized with digitonin. Analytical Biochemistry 1984, 137: 360-367. (Year: 1984).*
Combined Chinese Office Action and Search Report issued Aug. 11, 2023, in corresponding Chinese Patent Application No. 201980067835.X (with English Translation and English Translation of Category of Cited Documents) 14 pages.
Wang Tian et al., "Mitochondrial Donation—Polar Body Genome Transfer for Preventing the Transmission of Inherited Mitochondrial Diseases" Chinese Journal of Cell Biology, vol. 37, No. 4, Dec. 31, 2015, pp. 455-459 (with English Abstract and English Translation).
Extended European Search Report issued Jun. 24, 2022 in European Patent Application No. 19860822.6, 13 pages.

(Continued)

*Primary Examiner* — Christopher M Babic
*Assistant Examiner* — Jennifer S Spence
(74) *Attorney, Agent, or Firm* — Oblon, McClelland, Maier & Neustadt, L.L.P.

(57) ABSTRACT

Provided herein are a method for isolation and transplantation of intact mitochondria to a lymphoid organ (a primary lymphoid tissue or a secondary lymphoid tissue), a composition of cells prepared by using a method described herein, and a method for manufacturing cells described herein. In particular, provided herein are methods of isolating intact mitochondria from a donor cell. Also provided herein are methods of transplanting mitochondria into a recipient cell. In some aspects, the methods can be performed in vivo. Further provided are a composition of cells that include the cells prepared using the methods of the present invention.

6 Claims, 16 Drawing Sheets

(56) References Cited

FOREIGN PATENT DOCUMENTS

| WO | WO 2016/008937 | A1 | 1/2016 |
|---|---|---|---|
| WO | WO 2017/124037 | A1 | 7/2017 |
| WO | WO2017156362 | A1 | 9/2017 |
| WO | WO 2018/092839 | A1 | 5/2018 |

OTHER PUBLICATIONS

Yuma Yamada, et al., "Mitochondrial delivery of Coenzyme $Q_{10}$ via systemic administration using a MITO-Porter prevents ischemia/reperfusion injury in the mouse liver," Journal of Controlled Release, vol. 213, XP029259356, 2015, pp. 86-95.
Database Embase [Online], Database accession No. EMB-621235249 & European Heart Journal, vol. 38, Supplement 1, Aug. 1, 2017, 2 pages.
Database Embase [Online], Database accession No. EMB-622761701 & Cardiology in the Young, vol. 28, Supplement 1, Apr. 1, 2018, 2 pages.
Jenna L. Gollihue, et al., "Prospects for therapeutic mitochondrial transplantation," Mitochondrion, vol. 35, XP085093221, 2017, pp. 70-79.
Yukari Yasuzaki, et al., "Mitochondrial matrix delivery using MITO-Porter, a liposome-based carrier that specifies fusion with mitochondrial membranes," Biochemical and Biophysical Research Communications, vol. 397, XP027103936, 2010, pp. 181-186.
Eriko Kawamura, et al., "Targeted mitochondrial delivery of antisense RNA-containing nanoparticles by a MITO-Porter for safe and efficient mitochondrial gene silencing," Mitochondrion, vol. 49, XP085927202, 2019, pp. 178-188.
Hideki Maeda, et al., "Generation of somatic mitochondrial DNA-replaced cells for mitochondrial dysfunction treatment," Scientific Reports, vol. 11, XP055908870, 2021, 16 pages.
Daisuke Sasaki, et al., "Transplantation of MITO cells, mitochondria activated cardiac progenitor cells, to the ischemic myocardium of mouse enhances the therapeutic effect," Scientific Reports, vol. 12, XP055930419, 2022, 13 pages.
Yuma Yamada, et al., "Power of mitochondrial drug delivery systems to produce innovative nanomedicines," Advanced Drug Delivery Reviews, vol. 154-155, XP086396271, 2020, pp. 187-209.
Takao Tsujioka, et al., "Resveratrol-Encapsulated Mitochondria-Targeting Liposome Enhances Mitochondrial Respiratory Capacity in Myocardial Cells," International Journal of Molecular Sciences, vol. 23, No. 112, XP055930421, 2022, 10 pages.
International Search Report Issued Nov. 26. 2019 In PCT/JP2019/036011 (submitting English translation only), 3 pages.
Nunnari J., et al., "Mitochondria: In Sickness and in Health", Cell, vol. 148, Mar. 16, 2012, pp. 1145-1159.
Suomalainen, A., et al., "Mitochondria diseases: the contribution of organelle stress responses to pathology", Molecular Cell Biology, vol. 19, Feb. 2018, pp. 77-92.
Chinnery, P.F., et al., "Mitochondrial disease in adults: what's old and what's new?", EMBO Molecular Medicine, vol. 7, No. 12, 2015, pp. 1503-1512.
Smeitink, J.A., et al., "Mitochondrial medicine: Ametabolic perspective on the pathology of oxidative phosphorylation disorders", Cell metabolism, vol. 3, Jan. 9-13, 2006, pp. 9-13.
Mills, E.L., et al., "Mitochondria are the powerhouses of immunity", Nature Immunology, vol. 18, No. 5, May 2017, pp. 488-498.
Bertero, E., et al., "Calcium Signaling and Reactive Oxygen Species in Mitochondria", Circulation Research http://circires.shsjournals.org. May 11, 2018, pp. 1460-1478.
Burke, P.J., "Mitochondria, Bioenergetics and Apoptosis in Cancer", Trends in Cancer, Cell Press, vol. 2. No. 12. Dec. 2017. pp. 857-870.
Attardi, G., et al., "Complementation and segregation behavior of disease-causing mitochdrial DNA mutations in cellualr model systems", Biochimica et Biophysica Acta, vol. 1271, 1995, pp. 241-248.
Smith, P.M., et al., "Altering the balance betweeen healthy and mutated mitochondrial DNA", J. Inherit Metab Dis, vol. 34, 2011, pp. 309-313.
Chinnery, P.F., et al., "Molecular pathology of MELAS and MERRF: The relationship between mutatio load and clinical phenotypes", Brain, vol. 120, 1997, pp. 1713-1721.
Lin, Y.-F., et al., "Maintenance and propagation of a deleterious mitochondrial genome by the mitochondrial unfolded portein response", Nature, vol. 533, May 19, 2016, pp. 416-423.
Nargund, A.M., et al., "Mitochondrial and Nuclear Accumulation of the Transcription Factor ATFS-1 Promotes OXPHOS Recovery during the $UPRI^{mt}$", Molecular Cell, vol. 58, Apr. 2, 2015, pp. 123-133.
Tian, Y., et al., "Mitochondria UPR: A Double-Edge Sword", Trends In Cell Biology, Aug. 2016, vol. 26, No. 8, pp. 563-565.
Fiorese, C.J., et al., "The Transcription Factor ATF5 Medlates a Mammalian Mitochondrial UPR". Current Biology, vol. 26, Aug. 8, 2016, pp. 2037-2043 with cover page.
Cherry, A.B., et al.. "Induced Pluripotent Stem Cells with a Mitochondrial DNA Deletion", Stem Cells, vol. 31, 2013, pp. 1287-1297.
Chou, S.-J., et al., "Impaired ROS Scavenging System in Human Induced Pluripotent Stem Cells Generated from Patients with MERRF Syndrome", Nature Scientific Reports, Mar. 30, 2016, pp. 1-14.
Folmes, C.D.L., et al., "Disease-Causing Mitochondrial Heteroplasmy Segregated Within Induced Pluripotent Stem Cell Clones Derived from a Patient with MELAS", Stem Cells, vol. 31, 2013, pp. 1298-1308.
Fujikura, J., et al., "Induced pluripotent stem cells generated from diabetic patients with mitochondrial DNA A3243G mutation", Diabetologia, vol. 55, 2012, pp. 1889-1698.
Galera, T., et al., "Generation of a human IPSC line from a patient with Leigh syndrome", Stem Cell Research, vol. 16, 2016. pp. 63-66.
Kodaira, M., et al., "Impaired respiratory function in MELAS-induced pluripotent stem cells with high heteroplasmy levels", FEBS Open Bio, vol. 5, 2015, pp. 219-225.
Liang, D., et al., "Generation of MERRF patient-derived induced pluripotent stem cell line IMERRF-C7", Stem Cell Research, vol. 17, 2016, pp. 616-618.
Wahlestedt, M., et al., "Somatic Cells with a Heavy Mitochondrial DNA Mutational Load Render Induced Pluripotent Stem Cells with Distinct Differentiation Defects", Stem Cells, vol. 32, 2014, pp. 1173-1182.
Wu, Y.-T., et al., "Generation of an induced pluripotent stem cell (IPSC) line from a 40-year-old patient with the A8344G mutation of Mitochondrial DNA and MERRF (myoclonic epilepsy with ragged red fibers) syndrome". Stem Cell Research, vol. 27, 2018, pp. 10-14.
Yokota, M., et al., "Mitochondrial respiratory dysfunction caused by a heteroplasmic mitochondrial DNA mutation blocks cellular reprogramming", Human Molecular Genetics, vol. 24, No. 16, 2015, pp. 4698-4709.
Hsu. Y.-C., et al., "Mitochondrial resetting and metabolic reprogramming in induced pluripotent stem cells and mitochondrial disease modeling", Biochimica et Biophysica Acta, vol. 1860, 2016, pp. 686-893.
Hämäläinen, R.H., et al., "Tissue- and cell-type—specific manifestations of heteroplasmic mtDNA 3243A>G mutation in human induced pluripotent stem cell-derived disease model", PNAS, Sep. 3, 2013, pp. E3622-E3630.
Kang. E., et al., "Age-Related Accumulation of Somatic Mitochondrial DNA Mutations In Adult-Derived Human IPSCs", Cell Stem Cell, vol. 18, May 5, 2016, pp. 625-636 with cover page.
Tachibana, M., et al., "Human Embryonic Stem Cells Derived by Somatic Cell Nuclear Transfer", Cell, vol. 153, June 6. 2013, pp. 1228-1238.
Ma, H., et al, "Metabolic rescue in pluripotent cells from patients with mtDNA disease", Nature, vol. 524, Aug. 13, 2015, 18 pages.
Zhang. J., et al., "Pregnancy derived from human zygote pronuclear transfer in a patient who had arrested embryos after IVF", Reproductive BioMedicine Online, vol. 33, 2016, pp. 529-533.

(56) References Cited

OTHER PUBLICATIONS

Greenfield, A., et al., "Assisted reproductive technologies to prevent human mitochondrial disease transmission", Nature Biotechnology, vol. 35, No. 11, Nov. 2017, pp. 1059-1069.
Bredenoord, A.L., et al., "Mitochondrial Replacement Techniques: Remaining Ethical Challenges" Cell Stem Cell, vol. 21, Sep. 7, 2017. pp. 301-304.
López-Otín, C., et al., "The Hallmarks of Aging", Cell, vol. 153, Jun. 6, 2013, pp. 1194-1217.
Hayflick, L., "The Limited IN VITRO Lifetime of Human Diploid Cell Strains", Experimental Cell Research, vol. 37, 1965, pp. 614-636.
Harley, C.B., et al., "Telomeres shorten during ageing of human fibroblasts", Nature, vol. 345, May 31, 1990, pp. 458-460.
Bodnar, A.G., "Extension of Life-Span by Introduction of Telomerase into Normal Human Cells", Science, vol. 279, Jan. 16, 1998, pp. 349-352 with cover page.
Sahin, E., et al., "Telomere dysfunction induces metabolic and mitochondrial compromise", Nature, vol. 470, Feb. 17, 2011. pp. 359-365 with cover page.
Sahin, E., et al., "Axis of ageing: telomeres, p53 and mitochondria", Molecular Cell Biology, Nature Reviews, vol. 13, Jun. 2012, pp. 397-404.
Alexeyev. M.F., "Is there more to aging than mitochondrial DNA and reactive oxygen species?", The FEBS Journal, vol. 276, 2009, pp. 5768-5787.
Kauppila, T.E.S., et al., "Mammalian Mitochondria and Aging: An Update", Cell Metabolism, vol. 25, Jan. 10, 2017, pp. 57-71.
Gomes, A.P., et al., "Declining $NAD^+$ Induces a Pseudohypoxic State Disrupting Nuclear-Mitochondrial Communication during Aging", Cell, vol. 155, Dec. 19, 2013, pp. 1624-1638.
Kuilman, T., et al., "Senescence-messaging secretome: SMS-ing cellular stress", Cancer, Nature Reviews, vol. 9, Feb. 2009, pp. 81-94.
Coppé, J.-P., et al., "Senescence-Associated Secretory Phenotypes Reveal Cell-Nonautonomous Functions of Oncogenic RAS and the p53 Tumor Suppressor", PLOS Biology, vol. 6. No.12, Dec. 2006, pp. 2854-2868.
Kang. C., et al., "The DNA damage response induces inflammation and senescence by inhibiting autophagy of GATA4", Science, vol. 349, No. 6255, Sep. 25, 2015, pp. aaa5612-1-aaa5612-11 with cover pages.
Correia-Melo, C., et al., "Mitochondria are required for pro-aging features of the senescent phenotype", The EMBO Journal, vol. 35, 2016, pp. 724-742.
Barritt. J.A., et al., "Epigenetic and experimental modifications in early mammalian development: Part II", Human Reproduction Update, vol. 7, No. 4, 2001, pp. 428-435.
Barritt, J.A., et al., "Mitochondria in human offspring derived from ooplasmic transplantation", Human Reproduction, vol. 16, No. 3, 2001, pp. 513-516.
Labbadia, J., et al, "The Biology of Proteostasis in Aging and Disease", Annu. Rev. Blochem., vol. 84, 2015, pp. 435-464 with cover page.
Vilchez, D., et al., "The role of protein clearance mechanisms in organismal ageing and age-related diseases", Nature Communications. vol. 5, Dec. 6, 2014, pp. 1-13.
Brehme, M., et al., "A Chaperome Subnetwork Safeguards Proteostasis in Aging and Neurodegenerative Disease", Cell Reports, vol. 9, Nov. 6, 2014, pp. 1135-1150 with supplemental information and cover page.
Chondrogianni, N., et al., "Profeasome activation: An innovative promising approach for delaying aging and retarding age-related diseases", Ageing Research Reviews, vol. 23, 2015, pp. 37-55.
Madeo, F., et al., "Essential role for autophagy in life span extension", The Journal of Clinical Investigation, JCI, vol. 125. No. 1, Jan. 2015, pp. 85-93 with cover page.
Melber, A., et al., "$UPR^{mt}$ regulation and output: a stress response mediated by mitochondrial-nuclear communication", Cell Research, vol. 28, 2018, pp. 281-295.

Mercer, J., et al., "Virus entry by macropinocytosis", Nature Cell Biology, vol. 11, No. 5, May 2009, pp. 510-520.
Amyere, M., et al., "Origin, originality, functions, subversions and molecular signalling of macropincytosis", Int. J. Med. Microbiol., vol. 291, 2002, pp. 487-494.
Pace II, J.K., et al., "Repeated horizontal transfer of a DNA transposon in mammals and other tetrapods", PNAS, Nov. 4, 2008, vol. 105, No. 44, pp. 17023-17028.
Rustom, A., et al., "Nanotubular Highways for Intercellular Organelle Transport", Science, vol. 303, Feb. 13, 2004, pp. 1007-1010 with cover page.
Kitani, T., et al., "Internalization of isolated functional mitochondria: involvement of micropinocytosis", J. Cell. Mol. Med., vol. 18, vol. 8, 2014, pp. 1694-1703.
Palm, W., et al., "The Utilization of Extracellular Proteins as Nutrients Is Suppressed by mTORC1", Cell, vol. 162, Jul. 16, 2015, pp. 259-270.
Gonzalez, A., et al., "Nutrient sensing and TOR signaling in yeast and mammals", The EMBO Journal, vol. 36 No. 4, 2017, pp. 397-408.
King, M.P., et al., "Human Cells Lacking mtDNA: Repopulation with Exogenous Mitochondria by Complementation", Science, Oct. 27, 1989, vol. 246, pp. 500-503.
Ji. P., et al., "Enucleation of cultured mouse fetal erythroblasts requires Rac GTPases and mDia2", Nature Cell Biology. vol. 10. no.3, Mar. 2008, pp. 314-321 with supplemental information.
Bayona-Bafaluy, M.P., et al., "A chemical enucleation method for the transfer of mitochondrial DNA to p° cells", Nucleic Acids Research, 2003, vol. 31 No. 16, pp. 1-4.
Ghosh, S.S., et al., "Use of Cytoplasmic Hybrid Cell Lines for Elucidating the Role of Mitochondrial Dysfunction in Alzheimer's Disease and Parkinson's Disease", Annals New York Academy of Sciences, 1999, pp. 176-191.
Tan, A.S., et al., "Mitochondrial Genome Acquisition Restores Respiratory Function and Tumorigenic Potential of Cancer Cells without Mitochondrial DNA", Cell Metabolism, vol. 21, Jan. 6, 2015, pp. 81-94.
Kukat, A., et al., "Generation of p° cells utilizing a mitochondrially targeted restriction endonuclease and comparative analysis", Nucleic Acids Research, 2008, vol. 36, No. 7, pp. 1-10.
Tanaka, M., et al., "Gene Therapy for Mitochondrial Disease by Delivering Restriction Endonuclease SmaI into Mitochondria", Journal of Biomedical Science, 2002, vol. 9, pp. 534-541.
Kim, M.J., et al., "Delivery of exogenous mitochondria via centrifugation enhances cellular metabolic function", Nature Scientific Reports, Feb. 20, 2018, vol. 8, pp. 1-13.
Rameplt, H., et al., "Coordination of Two Genomes by Mitochondrial Translational Plasticity", Cell, vol. 167, Oct. 6, 2016, pp. 308-310.
Quirós, P.M., et al., "Mitonuclear communication in homeostasis and stress", Molecular Cell Biology, vol. 17, Apr. 2016, pp. 213-226.
Kong, B.-W., et al., "Expression analysis and mitochondrial targeting properties of the chicken manganese-containing superoxide dismutase", Biochimica et Biophysica Acta, vol. 1625, 2003, pp. 98-108.
Szeto, H.H., et al., "Novel Therapies Targeting Inner Mitochondrial Membrane—From Discovery to Clinical Development", Parm. Res., 2011, vol. 28, pp. 2669-2679.
Weissig, V., et al., "DQAsome/DNA complexes release DNA upon contact with Isolated mouse liver mitochondria", Journal of Controlled Release, vol. 75, 2001, pp. 401-408.
Yamada, Y., et al., "MITO-Porter: A liposome-based carrier system for delivery of macromolecules into mitochondria via membrane fusion", Science Direct, Biochimica et Biophysica Acta, vol. 1778, 2008, pp. 423-432.
Yamada, Y., et al., "Dual Function MITO-Porter, a Nano Carrier Integrating Both Efficient Cytoplasmic Delivery and Mitochondrial Macromolecule Delivery", The American Society of Gene & Cell Therapy, Molecular Therapy, vol. 19, No. 8, Aug. 2011, pp. 1449-1456.
Kawamura, E., et al., "Mitochondrial targeting functional peptides as potential devices for the mitochondrial delivery of a DF-MITO-Porter", Mitochondrion, vol. 13, 2013, pp. 610-614.

(56) References Cited

OTHER PUBLICATIONS

Kruse, S.E., et al., "Mice with Mitochondrial Complex I Deficiency Develop a Fatal Encephalomyopathy", Cell Metabolism, vol. 7, Apr. 2008, pp. 312-320.
Pinto, M., et al., "Transient mitochondrial DNA double strand breaks in mice cause accelerated aging phenotypes in a ROS-dependent but p53/p21-independent manner", Cell Death and Differentiation, vol. 24, 2017, pp. 288-299.
Dai, Y., et al., "Behavioral and metabolic characterization of heterozygous and homozygous POLG mutator mice", Mitochondrion, vol. 13, 2013, pp. 282-291.
Zhang, R., et al., "Independent impacts of aging on mitochondrial DNA quantity and quality in humans", BMC Genomics, vol. 18, 2017, pp. 1-14.
Lynch, H.E., et al., "Thymic involution and immune reconstitution", Cell. Trends in Immunology, vol. 30, No. 7, Jun. 2009, pp. 366-373.
Doulias. P.-T., et al., "Nitric Oxide Regulates Mitochondrial Fatty Acid Metabolism Through Reversible Protein S-Nitrosylation", Science Signaling, vol. 6, No. 256, Jan. 1, 2013, pp. 1-8.
Griffith, A.V., et al., "Metabolic Damage and Premature Thymus Aging Caused by Stromal Catalase Deficiency", Cell Reports, vol. 12, Aug. 18, 2015, pp. 1071-1079 with cover pages.
Taub, D.D., et al., "Insights into thymic aging and regeneration", Immunological Reviews, vol. 205, 2005, pp. 72-93.
Jung, W.-S., et al., "Stimulatory effect of HGF-overexpressing adipose tissue-derived mesenchymal stem cells on thymus regeneration in a rat thymus involution model", Cell Biology International, vol. 38, 2014, pp. 1106-1117.
Morrison, T.J., et al., "Mesenchymal Stromal Cells Modulate Macrophages in Clinically Relevant Lung Injury Models by Extracellular Vesicle Mitochondrial Transfer", Am. J., Respir. Crit Care Med., 2017, vol. 196, pp. 1275-1286.
Abe, J., et al., "Cardiac progenitor cells activated by mitochondrial delivery of resveratrol enhance the survival of a doxorubicin-induced cardiomyopathy mouse model via the mitochondrial activation of a damaged myocardium", Journal of Controlled Release, vol. 269, 2018, pp. 177-188.
Pannicke, U., et al., "Reticular dysgenesis (aleukocytosis) is caused by mutations in the gene encoding mitochondrial adenylate kinase 2", Nature Genetics, vol. 41, No. 1, 2009, pp. 101-105.
Obukhova, L.A., et al., "Mitochondria-targeted antioxidant SkQ1 Inhibits age-dependent involution of the thymus is normal and senescence-prone rats", Aging, Apr. 2009, vol. 1 No. 4, pp. 389-401.
Obukhova, L.A., et al., "Structural and Functional Basis of Accelerated Involution of the Thymus in OXYS Rats", Advances in Gerontology, vol. 4, No. 1, 2014, pp. 16-21.
Quintana, A., et al., "Sustained Activity of Calcium Release-activated Calcium Channels Requires Translocation of Mitochondria to the Plasma Membrane", Journal of Biological Chemistry, vol. 281, No. 52, 2006, pp. 40302-40309 with cover page.
Case, A.J., et al., "Heightened Susceptibility to Influenza Mortality in Immunodeficient Mice Caused by a T-Cell Specific Defect in SOD2", Blood, vol. 114, 2009, 2 pages (submitting English abstract only).
De Barros, S.C., et al., "Concise Review: Hematopoietic Stem Cell Transplantation: Targeting the Thymus", Stem Cells, vol. 31, 2013, pp. 1245-1251.
Rocca, C.J., et al., "Transplantation of wild-type mouse hematopoietic stem and progenitor cells ameliorates deficits in a mouse model of Friedreich's ataxia", Science Translational Medicine, vol. 9, Oct. 2017, pp. 1-12 with cover page.
Office Action issued Oct. 3, 2023, in corresponding Japanese Patent Application No. 2020-546212, 7 pages.
Office Action issued Jul. 27, 2024, in Chinese Application No. 201980067835X with English Translation.
Office Action issued Oct. 21, 2024, in corresponding China Patent Application No. 201980067835.X, 5 pages.
G. A. Shilovsky et al., (2015), "Thymic Involution in Ontogenesis: Role in Aging Program", vol. 80, No. 12 pp. 1629-1631.

* cited by examiner

Spleens of 3-weeks-old Ndufs4 KO mice

Analysis results of spleens of three female littermate mice with different genotypes Evaluation of growth and differentiation capability of hematopoietic progenitor cells in bone marrow of Ndufs4 KO mice Bone marrow transplantation experiment on Ndufs4 KO mice as recipients Comparison of lifetimes between homozygous mice with and without bone marrow transplantation Comparison of survival periods between Ndufs4 KO mice with and without bone marrow transplantation Confirmation of engraftment after bone marrow transplantation

TRANSPLANTATION OF MITOCHONDRIA INTO LYMPHOID ORGAN AND COMPOSITION THEREFOR

TECHNICAL FIELD

I. Field of the Invention

The present invention provides methods for isolation and transplantation of mitochondria into lymphoid organs, composition of cells prepared using the methods described herein, and methods for manufacturing the cell described herein.

BACKGROUND ART

II. Background of the Invention

Impaired mitochondrial function, for example impairment of the respiratory chain complex, is an important cause of mitochondrial disease and aging. Reduced mitochondrial function can affect the cells in many of the major organs that are associated with mitochondrial disease and age-related disorders. In addition, dysfunction of mitochondria can effect energy metabolism of immunocompetent cells. For example, the monocytic macrophages and dendritic cells involved in innate immunity depend mainly on mitochondria-independent anaerobic glycolysis for energy. It has also been shown that memory T cells and regulatory T cells depend on oxidative phosphorylation (OXPHOS) through fatty acid oxidation. Furthermore, decreased T cell function along with aging has been reported as a typical sign of so-called immune senescence.

SUMMARY OF THE INVENTION

III. Summary of the Invention

This application addresses the unmet need to enhance or improve the function of lymphoid organs, such as the thymus, through the isolation and transfer of mitochondria. In addition, this invention addresses an unmet need for the transplantation of isolated mitochondria into both adherent and floating cells.

The present invention confirmed thymic atrophy and decrease in adaptive immune cells in Ndufs4 knockout mice. Ndufs4 is a gene encoding a subunit of mitochondrial respiratory chain complex I, and an abnormality on this gene causes loss of function of mitochondrial respiratory chain complex I. Against this, local administration of mitochondria into the thymus resulted in a wide distribution of the mitochondria over the thymic tissues. The thymus is an important organ responsible for development of adaptive immune cells. In particular, T cells are generated in the thymus and matured in the thymus. Therefore, it is considered that intrathymic administration of mitochondria alleviates at least partially an abnormality in adaptive immunity particularly caused by T cell abnormalities.

In some embodiments, the method comprises (a) purifying isolated mitochondria from a donor cell; (b) co-culturing the isolated mitochondria with one or more peptides comprising a membrane transfer sequence for a period of time sufficient to generate isolated mitochondria expressing a membrane transfer sequence; and (c) transplanting an intact exogenous mitochondria into a recipient cell comprising transplanting the isolated mitochondria expressing a membrane transfer sequence into a recipient cell. In some embodiments, the one or more peptides can include a membrane transfer sequence that is a cell membrane permeable peptide, a mitochondrial membrane fusogenic peptide, or both.

In some embodiments, the one or more peptides is a peptide conjugate. In some embodiments, the peptide conjugate comprises a peptide and a lipid. In some embodiments, the lipid is attached to an N-terminus of the peptide. In some embodiments, the lipid is attached to a C-terminus of the peptide. In some embodiments, the lipid allows the peptide to embed into a mitochondrial membrane.

Some embodiments, further include co-culturing the isolated mitochondria with one or more moieties. In some embodiments, the one or more moieties includes polyethylene glycol. In some embodiments, the one or more moieties includes an aptamer.

Some embodiments further include activating the mitochondria from a donor cell before isolating the mitochondria. In some embodiments, activating the mitochondria is performed using a mitochondria-directed carrier (e.g., MITO-Porter) encapsulating a chemical agent. In some embodiments, the chemical agent is selected from the group consisting of coenzyme Q10 (CO-Q-10), resveratrol, nicotinamide riboside, n-acetyl cysteine, alpha-tocopherol, omega-3 fatty acid, glucosamine, creatine monohydrate, acetyl l-carnitine, epicatechin, quercetin, an autophagy inducer, and an apoptosis inhibitor. Coenzyme Q10 may be a reduced form.

In some embodiments, the donor cell is from an organ that can include a thymus, a spleen, a lymph node, a heart, a lung, a pancreas, a liver, skin, a kidney, blood, a muscle, or a lymphatic vessel. In some embodiments, the donor cell is selected from the group consisting of a fibroblast, a hepatocyte, a platelet, a myocyte, and an inducible pluripotent stem cell (iPSC). In some embodiments, the donor cell comprises cells that are autogenic or allogenic.

In some embodiments, the recipient cell is a cell from an organ that includes a thymus, a spleen, a lymph node, a heart, a lung, a pancreas, a liver, skin, a kidney, blood, a lymphatic vessel, an eye, a nose or an ear. In some embodiments, the recipient cell is an inducible pluripotent stem cell (iPSC). In some embodiments, the recipient cell is from a host with an age related disease. In some embodiments, recipient cells are derived from an aged host (e.g., a 40 years or more old host, a 45 years or more old host, a 50 years or more old host, a 55 years or more old host, a 60 years or more old host, a 65 year or more old host, and a 70 year or more old host). In other embodiments, the recipient cell is from a host with a mitochondrial disease. In some embodiments, the recipient cell is in an intact organ selected from the group consisting of a thymus, a spleen, a lymph node, a heart, a lung, a pancreas, a liver, skin, a kidney, blood, bone marrow, synovium, a lymphatic vessel, a brain, an eye, a nose and an ear.

In some embodiments, further include performing the transplantation in vivo. In some embodiments, performing in vivo transplantation includes a mitochondria-directed carrier (e.g., MITO-Porter). In some embodiments, the mitochondria-directed carriers (e.g., MITO-Porter) contain one or more peptides attached to the surface of the mitochondria-directed carrier (e.g., MITO-Porter). In some embodiments, one or more peptides attached to the surface of the mitochondria-directed carrier (e.g., MITO-Porter) is identical with one or more peptides used for co-culturing with isolated mitochondria. In some embodiments, the mitochondria-directed carrier (e.g., MITO-Porter) contains at least one chemical agent selected from the group consisting of CO-Q-10, resveratrol, nicotinamide riboside, n-acetyl cysteine, alpha-tocopherol, omega-3 fatty acid, glucosamine, creatine monohydrate, acetyl l-carnitine, epicatechin, quercetin, an autophagy inducer, and an apoptosis inhibitor.

In some embodiments, the transplantation is made into an organ selected from the group consisting of a heart, a liver, an ear, an eye, a thymus, a brain, a lung, an endothelial cell, lymph nodes, bone marrow, blood, a lymphatic vessel, a nose, a spleen and a synovium. In some embodiments, the transplantation is made into an organ selected from the group consisting of a thymus, a spleen and bone marrow. In some embodiments, the transplantation is made into a primary lymphoid tissue. In some embodiments, the transplantation is made into a secondary lymphoid tissue. The primary lymphoid tissues include bone marrow and a thymus, and the secondary lymphoid tissues include a spleen, a lymph node, and Peyer's patch.

In some embodiments, the transplantation is performed using interventional radiology (IVR)-computed tomography (CT). In specific embodiments, the IVR-CT is X-Ray CT.

In some embodiments, the transplantation is via intra-thymic injection.

In some embodiments, further include using post-transplantation support.

In some embodiments, the post-transplantation support includes a proper physical exercise, or a defined way of respiration.

In one aspect, provided are a composition of cells prepared using the methods of provided herein.

In another aspect, provided are methods of manufacturing the cells prepared using any one of the methods described herein.

In the present invention, the following embodiments may also be provided.

[1] A method of transplanting intact exogenous mitochondria into a recipient cell, comprising:
  (a) purifying isolated mitochondria from a donor cell;
  (b) co-culturing the isolated mitochondria with one or more peptides comprising a membrane transfer sequence for a period of time sufficient to generate isolated mitochondria expressing a membrane transfer sequence; and
  (c) transplanting the isolated mitochondria expressing a membrane transfer sequence into a recipient cell.

[2] The method according to [1], wherein the one or more peptides comprising a membrane transfer sequence are selected from the group consisting of a cell membrane permeable peptide and a mitochondrial membrane fusogenic peptide.

[3] The method according to [1] or [2], wherein the one or more peptides is a peptide conjugate.

[4] The method according to [3], wherein the peptide conjugate comprises a peptide and a lipid.

[5] The method according to [4], wherein the lipid is attached to an N-terminus of the peptide.

[6] The method according to [4], wherein the lipid is attached to a C-terminus of the peptide.

[7] The method according to any one of [4] to [6], wherein the lipid allows the peptide to embed into a mitochondrial membrane.

[8] The method according to any one of [1] to [7], further comprising co-culturing the isolated mitochondria with one or more moieties.

[9] The method according to [8], wherein the one or more moieties comprises polyethylene glycol.

[10] The method according to [8], wherein the one or more moieties comprises an aptamer.

[11] The method according to any one of [1] to [10], further comprising activating the mitochondria from the donor cell before isolating the mitochondria.

[12] The method according to [11], wherein activating the mitochondria is performed using a mitochondria-directed carrier (e.g., MITO-Porter) encapsulating a chemical agent.

[13] The method according to [12], wherein the chemical agent is selected from the group consisting of CO-Q-10, resveratrol, nicotinamide riboside, n-acetyl cysteine, alpha-tocopherol, omega-3 fatty acid, glucosamine, creatine monohydrate, acetyl l-carnitine, epicatechin, quercetin, an autophagy inducer, and an apoptosis inhibitor.

[14] The method according to any one of [1] to [13], wherein the donor cell is from an organ selected from the group consisting of a thymus, a spleen, a lymph node, a heart, a lung, a pancreas, a liver, skin, a kidney, blood, a muscle, and a lymphatic vessel.

[15] The method according to any one of [1] to [14], wherein the donor cell is selected from the group consisting of a fibroblast, hepatocyte, a platelet, a myocyte, and an inducible pluripotent stem cell (iPSC).

[16] The method according to any one of [1] to [15], wherein the donor cell comprises cells that are autogenic or allogeneic.

[17] The method according to any one of [1] to [16], wherein the recipient cell is a cell from an organ selected from the group consisting of a thymus, a spleen, a lymph node, a heart, a lung, a pancreas, a liver, skin, a kidney, blood, a lymphatic vessel, an eye, a nose and an ear.

[18] The method according to any one of [1] to [17], wherein the recipient cell is an inducible pluripotent stem cell (iPSC).

[19] The method according to any one of [1] to [18], wherein the recipient cell is from a host with an age related disease.

[20] The method according to any one of [1] to [19], wherein the recipient cell is from a host with a mitochondrial disease.

[21] The method according to any one of [1] to [20], wherein the recipient cell is in an intact organ selected from the group consisting of a thymus, a spleen, a lymph node, a heart, a lung, a pancreas, a liver, skin, a kidney, blood, bone marrow, synovium, a brain, a lymphatic vessel, an eye, a nose and an ear.

[22] The method according to any one of [1] to [21], further comprising performing the transplantation in vivo.

[23] The method according to [22], wherein performing the in vivo transplantation includes a mitochondria-directed carrier (e.g., MITO-Porter).

[24] The method according to, wherein the mitochondria-directed carrier (e.g., MITO-Porter) contains one or more peptides attached to the surface of the mitochondria-directed carrier (e.g., MITO-Porter).

[25] The method according to [24], wherein the one or more peptides attached to the surface of the mitochondria-directed carrier (e.g., MITO-Porter) is identical with one or more peptides used for co-culturing with the isolated mitochondria.

[26] The method according to any one of [23]-[25], wherein the mitochondria-directed carrier (e.g., MITO-Porter) contains at least one chemical agent selected from the group consisting of CO-Q-10, resveratrol, nicotinamide riboside, n-acetyl cysteine, alpha-tocopherol, omega-3 fatty acid, glucosamine, creatine monohydrate, acetyl carnitine, epicatechin, quercetin, an autophagy inducer, and an apoptosis inhibitor.

[27] The method according to any one of [22]-[26], wherein the transplantation is performed in an organ selected from the group consisting of a heart, a liver, an ear, an eye, a thymus, a brain, a lung, an endothelial cell, a lymph node, bone marrow, blood, a kidney, a lymphatic vessel, a nose, a spleen, and a synovium.

[28] The method according to any one of [22] to [27], wherein the transplantation is performed using interventional radiology (IVR)-computed tomography (CT).

[29] The method according to, wherein the IVR-CT is X-Ray CT.

[30] The method according to any one of [22] to [29], wherein the transplantation is via intra-thymic injection.

[31] The method according to any one of [1] to [30], further comprising performing post-transplantation support.

[32] The method according to [31], wherein the post-transplantation support includes a proper physical exercise, or a defined way of respiration.

[33] A composition of cells prepared using the methods according to any one of [1] to [32].

[34] A method of manufacturing the cells prepared using any one of the methods according to [1] to [33].

The present invention also provides the following embodiments.

[1A] A pharmaceutical formulation containing mitochondria to be administered to at least one tissue selected from the group consisting of a primary lymphoid tissue and a secondary lymphoid tissue.

[2A] The pharmaceutical formulation according to [1A], wherein the mitochondria are isolated mitochondria.

[3A] The pharmaceutical formulation according to [1A] or [2A], wherein the mitochondria are treated with a mitochondrial activator.

[4A] The pharmaceutical formulation according to [1A], wherein the mitochondria are in an intracellular form.

[5A] The pharmaceutical formulation according to [4A], wherein the cell is a non-immune cell.

[6A] The pharmaceutical formulation according to [5A], wherein the cell is a cell selected from the group consisting of a cardiac stem cell and a cardiac progenitor.

[7A] The pharmaceutical formulation according to [4A], wherein the cell is an immune cell subjected to mitochondrial activation treatment.

[8A] The pharmaceutical formulation according to [4A] or [7A], wherein the cell is an immune cell having a MITO-Porter.

[9A] The pharmaceutical formulation according to any one of [1A]-[8A], wherein a subject to which the pharmaceutical formulation is to be administered has mitochondria with functional abnormality.

[10A] Use of mitochondria in manufacturing a pharmaceutical formulation containing mitochondria, wherein the pharmaceutical formulation is to be administered to at least one tissue selected from the group consisting of a primary lymphoid tissue and a secondary lymphoid tissue.

[11A] The use according to [10A], wherein the mitochondria are isolated mitochondria.

[12A] The use according to [10A] or [11A], wherein the mitochondria are treated with a mitochondrial activator.

[13A] The use according to [10A], wherein the mitochondria are in an intracellular form.

[14A] The use according to [10A], wherein the cell is a non-immune cell.

[15A] The use according to [10A], wherein the cell is a cell selected from a cardiac stem cell and a cardiac progenitor cell.

[16A] The use according to [10A], wherein the cell is an immune cell subjected to mitochondrial activation treatment.

[17A] The use according to [13A] or [16A], wherein the cell is an immune cell having a MITO-Porter.

[18A] The use according to any one of [10A]-[17A], wherein a subject to which the pharmaceutical formulation is to be administered has mitochondria with functional abnormality.

DETAILED DESCRIPTION OF THE INVENTION

IV. Detailed Description of the Invention

Figure 1:
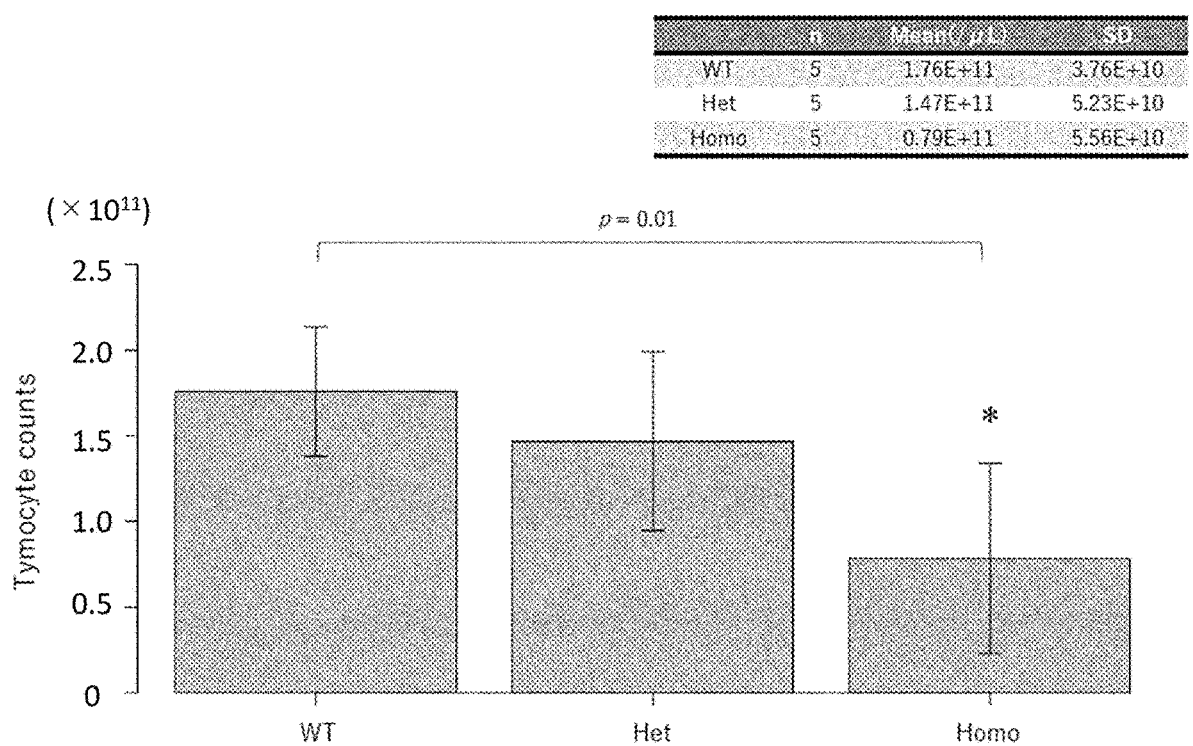
FIG. 1 shows comparison of the cell number in the thymus in wild types (WT), Ndufs4 heterozygous knockout mice (Het), and Ndufs4 homozygous knockout mice (Homo).

As provided herein, this invention relates to the improvement in the quality and quantity of immune cells, such as T-cell, by transplanting healthy mitochondria with less genetic mutations into lymphoid organs, such as the thymus, in order to restore the function of the target immune cells and promote a healthy immune system. Accordingly, the improved immune cells can ameliorate mitochondrial and age-related diseases.

4.1 Preparation of Highly Purified Mitochondria

As disclosed herein, preparation of isolated mitochondria with high quality and high purity can be performed by extracting cells from donor tissue and culturing them in large quantity. The methods provided herein enable the integrated mitochondrial transplantation (IMiT). In some embodiments, the mitochondria are initially isolated. The isolated mitochondria desirably have membrane potential in mitochondrial inner membrane. As used herein, the term "isolation" refers to taking mitochondria out from the inside of a cell, as mentioned for mitochondria. As used herein, the term "purification" refers to improving degree of purification by further separating at least one component contaminating into the isolate.

To begin, cells can be extracted from donor tissue and cultured in large quantity. In some embodiments, the donor tissue will be from a healthy donor. In some embodiments, fibroblasts that can be cultured safely in large amount will be used rather than cells with high mitochondrial content per cell, such as hepatocytes, platelets, myocytes, or an iPSC. Fibroblasts can be obtained, for example, by a skin biopsy. Therefore, in some embodiments, a tissue biopsy is performed on a donor and a sufficient amount of fibroblasts are extracted. In specific embodiments, the tissue biopsy is from a tissue section that is about 4 mm in diameter. In other embodiments, fibroblasts are obtained from a commercially available source. In specific embodiments, the commercially available fibroblasts are prepared under Good Clinical Practice standards. In some embodiments, a tissue biopsy is performed on a donor and a sufficient amount of mesenchymal stem cells or cardiac stem cells (or cardiac progenitor cells) are extracted.

As disclosed herein, activation of mitochondria before isolation can yield higher quality mitochondria. Therefore, in some embodiments, mitochondrial function of fibroblasts is activated prior to isolation. In specific embodiments, the isolated high quality mitochondria are transplanted to a recipient cell with abnormal mitochondrial gene and respiratory chain complex activity. In yet further embodiments, the isolated high quality mitochondria are transplanted to a recipient cell with abnormal mitochondrial gene derived from maternal inheritance. In further embodiments, the isolated high quality mitochondria are transplanted to a recipient cell with abnormal mitochondrial gene originated from a nuclear gene.

One skilled in the art would understand how to activate mitochondria. A method for activating mitochondria can employ, for example, a method disclosed in WO2018/092839. Additionally, for example, in some embodiments, mitochondrial function can be activated by encapsulating CoQ-10 within mitochondria-directed carriers (e.g., MITO-Porters) and co-culturing them with donor cells (e.g., fibroblasts). In some embodiments, the mitochondria-directed carrier (e.g., MITO-Porter) can encapsulate a different chemical agent. Other agents that can activate mitochondria include, but are not limited to, CO-Q-10, resveratrol, nicotinamide riboside, n-acetyl cysteine, alpha-tocopherol, omega-3 fatty acid, glucosamine, creatine monohydrate, acetyl l-carnitine, epicatechin, quercetin, an autophagy inducer, and an apoptosis inhibitor.

The mitochondria-directed carrier may be a vesicle that displays a mitochondria-directed molecule on the membrane surface, and the vesicle may be, for example, a liposome that consists of lipid bilayer membrane, and may be a liposome that contains dioleylphosphatidyl ethanolamine (DOPE) and phosphatidic acid (PA) and/or sphingomyelin (SM) as components. Examples of the mitochondria-directed molecule include polypeptides such as R8 peptide, mitochondria-targeted signal (MTS) peptide (Kong, B W. et al., Biochimica et Biophysica Acta 2003, 1625, pp. 98-108) and S2 peptide (Szeto, H. H. et al., Pharm. Res. 2011, 28, pp. 2669-2679); and liposoluble cationic substances such as Lipophilic triphenylphosphonium cation (TPP) and Rhodamine 123. In introduction of an agent into the vesicle (e.g., a liposome), the agent may be introduced by a chemical method such as ionic bonding, hydrophobic bonding, and covalent bonding between lipid composing the liposome and the agent, or the agent may be encapsulated within the lumen of the liposome by a common method. The mitochondria-directed carriers can also include mitochondria-directed liposomes such as DQAsome (Weissig, V. et al., J. Control. Release 2001, 75, pp. 401-408), MITO-Porter (Yamada, Y. et al., Biochim Biophys Acta. 2008, 1778, pp. 423-432), DF-MITO-Porter (Yamada, Y. et al., Mol. Ther. 2011, 19, pp. 1449-1456), and modified DF-MITO-Porter with modification of S2 peptide (Kawamura, E. et al., Mitochondrion 2013, 13, pp. 610-614). R8 peptide and S2 peptide are mitochondria-directed and cell-membrane-permeable peptides.

In some embodiments, high quality mitochondria can be isolated from the inside of a cell containing the mitochondria by enhancing membrane permeability of the cell using digitonin.

In further embodiments, the membrane transfer function is added to the surface of the outer membrane of mitochondria by co-culturing the isolated mitochondria and peptides with two membrane transfer sequences. In some embodiments, the two peptides are peptides comprising a membrane transfer sequence including a cell membrane permeable peptide and a mitochondrial membrane fusogenic peptide.

In other embodiments, the peptide is a peptide conjugate. The peptide conjugate can contain a peptide and a lipid. The lipid can be attached to an N-terminus of the peptide, a C-terminus of the peptide, or both. In certain aspects, the lipid allows the peptide to embed into a mitochondrial membrane.

Accordingly, in some embodiments the methods further include co-culturing the isolated mitochondria with one or more moieties. In some embodiments, the one or more moieties comprises polyethylene glycol. In other embodiments, the one or more moieties comprises an aptamer.

In some embodiments, the transfer of mitochondria is performed using trehalose buffer.

4.2.1 Transplantation of Separated or Isolated Mitochondria

Impaired mitochondrial function is an important cause of mitochondrial disease, immune abnormality, and aging. Many of the major organs can be effected by impaired mitochondrial function. In addition, impaired mitochondrial function can produce an imbalance in both innate and adaptive immunity, which can play an important role in the mitochondrial disease and aging.

Energy metabolism abnormalities have been reported in immunocompetent cells. The monocytic macrophages and dendritic cells involved in innate immunity depend mainly on mitochondria-independent anaerobic glycolysis for energy. Effector T cells involved in adaptive immunity also use mitochondrial oxidative phosphorylation (OXPHOS). Memory T cells and regulatory T cells depend on OXPHOS through fatty acid oxidation. Thus, immunocompetent cells with impaired mitochondrial function are expected to cause decreased adaptive immunity, particularly owing to reduced T cell activity. Indeed, decreased T cell function along with aging has been reported as a typical sign of so-called immune senescence.

In the thymus, early thymic progenitors differentiate from hematopoietic stem cells and grow into mature CD4 and CD8-expressing T cells through proliferation (up to one-million-fold) and differentiation, such as reconstitution of T cell receptor (TCR) genes, selection of T cells that express TCR-recognizing self-MHC (positive selection), and removal of T cells that express TCR recognizing self-antigen (negative selection). Thymic epithelial cells (TECs) in the thymic stroma of the medulla and cortex help in the differentiation of T cells in the thymus. In normal organ tissues, the epithelial cells are closely adhered and aligned like a sheet, while the TECs have a sponge-like structure. The early thymic progenitors proliferate, differentiate, and mature while moving from the cortex to the medulla between the TECs present in the three-dimensional structure, and then they move out of the thymus.

Cysteine S-nitrosylation that was subject to posttranslational modification using nitric oxide, a redox-related protein modification, was studied in mouse tissue, revealing that the thymus is a highly mitochondria-dependent organ, similar to the brain, heart, lung, liver, and kidneys. Therefore, decrease in mitochondrial function of TECs and T cells may cause abnormality in the T cell maturation process in the thymus and changes in T cell subsets, such as decreases in CD8+ T cells and CD4+ cells, decrease in CD4+ naive T cells, and increase in memory T cells, as well as possible abnormal expression of receptors on the T cells in the proliferation phase, similar to the aging immune system noted in thymus atrophy that might lead to attenuated immunological tolerance. In addition, the lymphocytes in the thymus are known to be most abundant during puberty (around teens), when the peak thymus weighs 30-40 g, followed by rapid regression that is almost depleted by 70 years of age.

Overproduction of reactive oxygen species (ROS) in the cortical stromal cells in the thymus has been implicated in thymic atrophy. Reduction of ATP production capacity due to decreased mitochondrial function in the thymic stromal cells, and overproduction of ROS may be major causes of thymic atrophy. Indeed, thymic regression has been observed from the early stage of growth in model animals that have temporally broken mitochondrial double-stranded DNA. Thymic atrophy is also observed in mice having mutated (mtDNA) replication enzyme DNA polymerase-gamma (POLG).

Accordingly, supporting the mitochondrial function of the TECs and T cells by transplanting healthy mitochondria with less genetic mutations to the thymus represents a novel approach to restore thymic function and delay thymic atrophy. Improvement in the quality and quantity of T cells can lead to a healthy immune system and is expected to have ameliorating effects on mitochondrial and age-related diseases.

In some embodiments, isolated mitochondria are prepared and a membrane transfer signal is added thereto. In this manner, the mitochondria with enhanced membrane permeability are then transferred to a cell. In some embodiments, highly purified isolated mitochondria are prepared and a high membrane transfer signal is added. The mitochondria with a high membrane transfer signal can then be transferred into a cell.

As disclosed herein, in some embodiments, mitochondria may be optionally activated within a donor cell before or after isolation of the mitochondria. As used herein, a treatment of activating mitochondria is referred to as "mitochondrial activation treatment". The treatments include use of a mitochondria-directed carrier (e.g., MITO-Porter) encapsulating a chemical agent so as to activate mitochondria, but various methods, not limited thereto, can be used. The chemical agent can be any agent that is capable of activating mitochondria. For example, the agent can be CO-Q-10, resveratrol, nicotinamide riboside, n-acetyl cysteine, alpha-tocopherol, omega-3 fatty acid, glucosamine, creatine monohydrate, acetyl-carnitine, epicatechin, quercetin, an autophagy inducer, or an apoptosis inhibitor. In some embodiments, the agent may be an electron donor for any one or more or all of mitochondrial respiratory chain complexes I, III, and IV. In some embodiments, the agent may be a substrate for any one or more or all of mitochondrial respiratory chain complexes I, III, and IV. In some embodiments, the agent may be a biocompatible antioxidant. In some embodiments, the agent may be resveratrol.

As disclosed herein, mitochondria can be isolated from a donor cell. In some embodiments, the donor cell is from an organ such as a spleen, a lymph node, a heart, a lung, a pancreas, a liver, skin, a kidney, blood, a muscle, and a lymphatic vessel. In specific embodiments, the donor cell is selected from the group consisting of a fibroblast, a hepatocyte, a platelet, a myocyte, and an iPSC. The donor cell can be either autogenic or allogeneic, but an autogenic or allogeneic donor cell can be appropriately selected depending on characteristics of abnormality of mitochondrial function in a recipient cell.

In some embodiments the recipient cell is from an organ, such as a thymus, a spleen, a lymph node, a heart, a lung, a pancreas, a liver, skin, a kidney, blood, a lymphatic vessel, an eye, a nose and an ear. In specific embodiments, the recipient cell is an inducible pluripotent cell (iPSC).

In specific embodiments two types of cells can be transplanted: adherent thymic epithelial cells (TECs), and floating thymic lymphocytes. In specific embodiments, the recipient cell is an adherent TEC, a floating thymic lymphocyte, or both. In other embodiments, the recipient cell is an adherent cell from a sold organ, such as cardiomyocytes in the heart, hepatocytes in the liver, and neurons in the brain.

Transplantation of the mitochondria from a donor cell to a recipient cell can help to improve the function of the recipient cell, including, but not limited to the mitochondrial function. Therefore, in some embodiments, the recipient cell is a cell in need of mitochondria with normal function or improved mitochondria. Accordingly, in some embodiments, the recipient cell is from a host with an age related disease. In other embodiments, the recipient cell is from a host with a mitochondrial disease.

In certain embodiments, the recipient cell can be in an intact organ. For example, the recipient cell can be from an organ such as a thymus, a spleen, a lymph node, a heart, a lung, a pancreas, a liver, skin, a kidney, blood, a lymphatic vessel, an eye, a nose and an ear, and the cell can be in the organ.

The improvement of mitochondrial function in the recipient cells after mitochondrial transplantation can be proportional to the number of donor mitochondria with normal function or donor mitochondria with high quality, which are taken up in the recipient cells. In some embodiments, recipient cells take up donor mitochondria by macropinocytosis. In specific embodiments, a peptide having a cell membrane transfer sequence is added to the donor mitochondria to improve mitochondrial uptake by macropinocytosis. For example, co-culture of MELAS cybrid cells with mitochondria that has a high membrane translocation signal added, can enable rapid and prolonged uptake of mitochondria. In even further embodiments, the uptake of exogenous mitochondria can enhance the function of endogenous mitochondria.

The optimal cell membrane transfer sequences differ depending on subject cell types. In some embodiments, the mitochondria can express one or more membrane transfer sequences that target one or more recipient cell types. For example, mitochondria can express a mixture of two or more different membrane transfer peptides that target epithelial cells, such as TECs, and floating thymic lymphocytes.

Mitochondria can also be transferred by somatic nuclear transfer. However, there is risk of immune rejection because of alloantigenicity caused by lack of consistent coordination between the nuclei and mitochondria after transplantation using somatic nuclear transfer. In mitochondrial transplantation, because the primary purpose is activation of the endogenous mitochondrial function and the mitochondria are transplanted locally, the risk of alloantigenicity is reduced. Therefore, in some embodiments, the transfer of intact autograft mitochondria into recipient cells is not immunogenic. In other embodiments, the transfer of intact allograft mitochondria into recipient cells is not immunogenic.

Damaged mitochondria may impair a cell. Therefore, as used herein, the word "intact" can mean that there is no or few damages to the extent as not impairing a cell. As used herein, "intact" can mean that physiologically normal functions are maintained. As used herein, the term "intact" can mean that mitochondria maintain outer membrane and inner membrane. As used herein, the term "intact" can mean that mitochondria (inner membrane thereof) have membrane potential. As used herein, the term "intact" can mean that mitochondria have no injury.

4.2.2 Transplantation of Isolated Cells

Mitochondria are contained within a cell. Therefore, mitochondrial transplantation is also achieved by transplanting cells. The Examples herein results that cell transplantation also widely distributed mitochondria over the thymus. The Example herein showed that mitochondria migrate intercellularly without remaining within a cell. Accordingly, transplantation of cells containing healthy mitochondria (e.g., healthy mitochondria with few genetic mutations) has an advantage equal to transplantation of mitochondria.

As disclosed herein, the cell may be activated prior to administration. The present invention may include use of a mitochondria-directed carrier (e.g., MITO-Porter) encapsulating a chemical agent, for activating mitochondria, but can employ various methods, not limited thereto, for activating mitochondria. The chemical agent may be any agent that can activate mitochondria. For example, the agent may be CO-Q-10, resveratrol, nicotinamide riboside, n-acetyl cysteine, alpha-tocopherol, omega-3 fatty acid, glucosamine, creatine monohydrate, acetyl carnitine, epicatechin, quercetin, an autophagy inducer, or an apoptosis inhibitor.

As disclosed herein, the cell to be administered may be derived from an organ or a tissue such as a thymus, a spleen, a lymph node, a heart, a lung, a pancreas, a liver, skin, a kidney, blood, a lymphatic vessel, an eye, a nose, and an ear. In some embodiments, the cell to be administered may be a tissue stem cell. In some embodiments, the cell to be administered may be a cardiac stem cell or a cardiac progenitor cell. In specific embodiments, either of the two types of the cells can be transplanted: an adherent thymus epithelial cell (TEC) and floating thymic lymphocyte. In specific embodiments, the cell to be administered is an adherent TEC, a floating thymic lymphocyte, or both. In other embodiments, the cell to be administered may be an adherent cell from a sold organ, such as a cardiomyocyte in the heart, a hepatocyte in the liver, and a neuron in the brain. The cells to be administered may be autologous or allogeneic to an individual to be administered.

As disclosed herein, cells to be administered may be a cell capable of providing mitochondria to a cell in a tissue to receive administration. Such cell can be confirmed by an assay for co-culturing cells in a tissue to receive administration and cells to be administered, and checking whether mitochondria would be provided from the cells to be administered to the cells in a tissue to receive administration. The cell capable of providing mitochondria, through co-culturing, to the cell in a tissue to receive administration can be used as the cell to be administered in the present invention. Whether the cell is capable of providing mitochondria or not can be checked by labelling mitochondria contained in the cell to be administered. The labeling of mitochondria may be made with a fluorescence label. As the fluorescence label, various labels capable of labeling mitochondria with fluorescence can be used. Prior to an assay, the cell to be administered may be subjected to mitochondrial activation treatment. In scme subjects, the cell to be administered may be a cardiac stem cell or a cardiac progenitor cell.

The present invention allows mitochondria to migrate intercellularly. Therefore, it is considered that a cell itself is not required to survive in an organ after transplantation. Accordingly, in some embodiments, cells to be administered to a primary lymphoid tissue and a secondary lymphoid tissue may be, for example, non-immune cells. The non-immune cells include a mature immune cell and an immature immune cell (e.g., a developing immune cell). In some embodiments, the cells to be administered to a primary lymphoid tissue and a secondary lymphoid tissue may also be, for example, non-hematopoietic stem cells, non-hematopoietic progenitor cells, non-lymphocytic common progenitor cells, non-NK cell/non-T-cell progenitor cells, non-myeloid common progenitor cells, non-granulocyte/macrophage progenitor cells, or may be non-macrophage-dendritic cell progenitor cells, and non-mast cell progenitor cells.

4.3 Methods and Sites for Transplantation

Hematopoietic stem cells have been reported to be safely injected directly into the thymus to differentiate into T-cells. In some embodiments, mitochondria or cells can be injected directly into the thymus tissue (e.g., stroma) of a subject (or a patient).

Therefore, in some embodiments, transplantation of mitochondria or cells can be made in vivo according to the method described herein. In some embodiments, in vivo transplantation includes transplantation with mitochondria-directed carriers (e.g., MITO-Porters), transplantation of mitochondria containing mitochondria-directed carriers, or transplantation of cells containing mitochondria-directed carriers. The mitochondria-directed carrier (e.g., MITO-Porter) can contain one or more peptides attached to the surface of the mitochondria-directed carrier (e.g., MITO-Porter).

The transplantation of the mitochondria or cells can be made into an organ or a tissue selected from the group consisting of a heart, a liver, an ear, an eye, a thymus, a brain, a lung, an endothelial cell, lymph nodes, bone marrow, blood, a spleen, a kidney, a lymphatic vessel, a nose, and a synovium. In specific embodiments, the transplantation of the mitochondria or cells can be made into an organ or a tissue selected from the group consisting of a thymus, a spleen, and bone marrow. In these embodiments, the transplantation of the mitochondria or cells can be made by injection into such organ or tissue (preferably, either tissue of a primary lymphoid tissue or a secondary lymphoid tissue; for example, an organ or a tissue selected from the group consisting of a thymus, a spleen, and bone marrow; e.g., a thymus).

In specific aspects, the mitochondria-directed carrier (e.g., MITO-Porter) can also include a chemical agent, such as but not limited to, CO-Q-10, resveratrol, nicotinamide riboside, n-acetyl cysteine, alpha-tocopherol, omega-3 fatty acid, glucosamine, creatine monohydrate, acetyl carnitine, epicatechin, quercetin, an autophagy inducer, and an apoptosis inhibitor.

Interventional radiology (IVR)-computed tomography (CT) is a therapeutic application of radiological diagnostic technology and supports treatment by inserting a puncture needle or a catheter into the body under CT guidance. Particularly, X-ray CT has improved not only in spatial and contrast resolution but also in time resolution, allowing real time puncture under CT observation. From the above, use of IVR-CT, such as X-ray CT, is considered to allow multiple intrathymic injections of isolated mitochondria or cells. In some embodiments, direct injection into the thymus can be performed using IVR-CT. In specific embodiments, direct injection into the thymus can be performed using X-ray CT.

In some embodiments, thymic atrophy can be alleviated and the differentiation and maturation of T cells can be promoted in the thymus by transfer of the intact mitochondria or cells. In some embodiments, the increase in T cells due to transplantation of mitochondria or cells can qualitatively and quantitatively correct abnormalities of T cells in peripheral blood. This may also lead to rejuvenation effect against immune senescence due to thymic atrophy.

In further embodiments, functional recovery of autoimmune T cell can lead to the improvement of disease state (recovery of immunological tolerance) by regulation of local innate and acquired immunity.

4.4 Post-Transplantation

In some embodiments, a scheduled rehabilitation is performed, in accordance with disease state, from the early stage after the transplantation to promote the improvement of transplant organ function. In specific embodiments, aerobic exercise is performed to significantly increase mitochondrial uptake and improve the function of the recipient cell.

Measurement of T cell function can be performed using methods known in the art. For example, in some embodiments mitochondrial function can be measured in the peripheral blood T cells.

4.5 Mitochondrial Formulations or Cell Formulations of the Present Invention

The present invention provides a pharmaceutical formulation containing mitochondria for administering to an organ or a tissue selected from the group consisting of a heart, a liver, an ear, an eye, a thymus, a brain, a lung, an endothelial cell, a lymph node, bone marrow, blood, a spleen, a kidney, a lymphatic vessel, a nose, and a synovium (preferably, either tissue of a primary lymphoid tissue or a secondary lymphoid tissue; for example, an organ or a tissue selected from the group consisting of a thymus, a spleen, and bone marrow; e.g., a thymus). The present invention also provides, in the pharmaceutical formulation of the present invention, a pharmaceutical formulation containing cells for administering to an organ or a tissue selected from the group consisting of a heart, a liver, an ear, an eye, a thymus, a brain, a lung, an endothelial cell, a lymph node, bone marrow, blood, a spleen, a kidney, a lymphatic vessel, a nose, and a synovium (preferably, either tissue of a primary lymphoid tissue or a secondary lymphoid tissue; for example, an organ or a tissue selected from the group consisting of a thymus, a spleen, and bone marrow; e.g., a thymus).

In some embodiments, the cells to be administered may be mitochondria or cells subjected to mitochondrial activation treatment, and the organ or tissue to receive administration may be an organ or a tissue selected from the group consisting of a heart, a liver, an ear, an eye, a thymus, a brain, a lung, an endothelial cell, a lymph node, bone marrow, blood, a spleen, a kidney, a lymphatic vessel, a nose, and a synovium (preferably, either tissue of a primary lymphoid tissue or a secondary lymphoid tissue; for example, an organ or a tissue selected from the group consisting of a thymus, a spleen, and bone marrow; e.g., a thymus).

In some embodiments, the cells to be administered may be cardiac stem cells or cardiac progenitor cells, and the organ or tissue to receive administration may be an organ or a tissue selected from the group consisting of a heart, a liver, an ear, an eye, a thymus, a brain, a lung, an endothelial cell, a lymph node, bone marrow, blood, a spleen, a kidney, a lymphatic vessel, a nose, and a synovium (preferably, either tissue of a primary lymphoid tissue or a secondary lymphoid tissue; for example, an organ or a tissue selected from the group consisting of a thymus, a spleen, and bone marrow; e.g., a thymus).

In some embodiments, the cells to be administered may be mitochondria or cardiac stem cells or cardiac progenitor cells subjected to mitochondrial activation treatment, and the organ or tissue to receive administration may be an organ or a tissue selected from the group consisting of a heart, a liver, an ear, an eye, a thymus, a brain, a lung, an endothelial cell, a lymph node, bone marrow, blood, a spleen, a kidney, a lymphatic vessel, a nose, and a synovium (preferably, either tissue of a primary lymphoid tissue or a secondary lymphoid tissue; for example, an organ or a tissue selected from the group consisting of a thymus, a spleen, and bone marrow; e.g., a thymus).

The pharmaceutical formulation of the present invention may be used for improving thymic function in a patient with functional abnormality in mitochondria. In this embodiment, the pharmaceutical formulation of the present invention may be intrathymically administered.

The pharmaceutical formulation of the present invention can be used for treating thymic atrophy in a patient with functional abnormality in mitochondria. In this embodiment, the pharmaceutical formulation of the present invention may be intrathymically administered.

The pharmaceutical formulation of the present invention may be used for improving bone marrow function in a patient with functional abnormality in mitochondria. In this embodiment, the pharmaceutical formulation of the present invention may be intramedullary administered.

The pharmaceutical formulation of the present invention may be used for improving immune function in a patient with functional abnormality in mitochondria. In this embodiment, the pharmaceutical formulation of the present invention may be locally administered to preferably, either tissue of a primary lymphoid tissue or a secondary lymphoid tissue, for example, an organ or a tissue selected from the group consisting of a thymus, a spleen, and bone marrow.

The pharmaceutical formulation of the present invention can be used for treating a patient with functional abnormality in mitochondria. In this embodiment, the pharmaceutical formulation of the present invention may be locally administered to an organ or a tissue selected from the group consisting of a heart, a liver, an ear, an eye, a thymus, a brain, a lung, an endothelial cell, a lymph node, bone marrow, blood, a spleen, a kidney, a lymphatic vessel, a nose, and synovium (preferably, either tissue of a primary lymphoid tissue or a secondary lymphoid tissue, for example, an organ or a tissue selected from the group consisting of a thymus, a spleen, and bone marrow; e.g., a thymus).

The pharmaceutical formulation of the present invention may contain mitochondria or cells and an excipient. The excipient is, for example, a pharmaceutically acceptable excipient. The pharmaceutically acceptable excipients include, but not particularly limited to, a pH adjuster, salt, a surfactant, a preservative, a stabilizer, and an isotonizing agent.

In certain aspects, provided is use of mitochondria or cells in manufacturing the pharmaceutical formulation of the present invention.

4.6 Subjects to be Administered with Mitochondria or Cells of the Present Invention As used herein, a subject or patient may be a mammal, and examples include primates such as a human and pet animals such as a dog and a cat. As used herein, the term "patient" means a subject having a disease or a diseased condition. According to the present invention, a subject to be administered with the mitochondria or cells of the present invention may be a subject having abnormality in mitochondrial function, for example, a mitochondrial disease patient. The mitochondrial disease patient may be a patient having abnormality in mitochondrial genome or a patient having abnormality in nuclear genome. The mitochondrial disease patient may be a patient with hereditary mitochondrial disease or a patient with acquired mitochondrial disease. According to the present invention, the subject to be administered with the mitochondria or cells of the present invention may be a subject having abnormality in mitochondrial function, and having an atrophying thymus. The thymic atrophy may be determined by comparing to a normal thymus belonging to an individual of the same age as the subject. According to the present invention, the subject to be administered with the mitochondria or cells of the present invention may be a subject having abnormality in mitochondrial function as well as having abnormality in immune function. The abnormality in mitochondrial function may be determined, for example, by comparing its mitochondrial membrane potential to membrane potential of a healthy subject.

EXAMPLES

Example 1: Detailed Analysis of Phenotypes of Ndufs4 Gene Knockout Mice

Ndufs4 gene is located on an autosome in human, and encodes 18 kDa of an accessory subunit (NADH: ubiquinone oxide reductase core subunit S4) of respiratory chain complex I (NADH: ubiquinone oxide reductase) in mitochondrial inner membrane. Mutation of Ndufs4 gene is involved in deficiency of mitochondrial respiratory chain complex I, which is autosomal recessive. This deficiency of the complex I has been considered to be the most frequent enzymatic defect in damage of oxidative phosphorylation in mitochondria. In this Example, it was found that thymuses in Ndufs4 knockout mice significantly atrophy relative to wildtype or heterozygous mice.

Peripheral blood of wildtype, heterozygous, and Ndufs4 knockout mice (each 4-weeks old, n=14-16) was individually taken and subjected to analysis of their blood components. Ndufs4 knockout mouse (The Jackson Laboratory, Stock No.: 027058) is as described in Kruse S E et al., Cell Metabolism, 7 (4): 312-320, 2008. The analysis results of the blood components were as shown in Table 1.

TABLE 1

Peripheral blood components of wildtype, heterozygous, and Ndufs4 knockout mice

Data of peripheral blood (4 weeks of age)

|  | WT (n = 15) | Ndufs4$^{+/-}$ (n = 14) | Ndufs4$^{-/-}$ (n = 16) |
|---|---|---|---|
| WBC (/mL) | 4840 ± 1650 | 4790 ± 1760 | 3720 ± 1580 (p = 0.06) |
| Gra (%) | 7.7 ± 4.0 | 7.4 ± 3.8 | 11.0 ± 7.3 |
| Mo (%) | 1.9 ± 2.2 | 2.1 ± 2.0 | 3.2 ± 3.0 |
| Lym (%) | 90.3 ± 4.4 | 90.5 ± 4.6 | 85.8 ± 7.0 * (p < 0.05) |
| CDF+ T (%) | 16.9 ± 3.8 | 17.2 ± 3.5 | 19.5 ± 7.9 |
| CD8+ T (%) | 8.4 ± 2.1 | 8.5 ± 1.7 | 10.8 ± 3.4 * (p < 0.05) |
| B (%) | 59.1 ± 5.5 | 56.2 ± 6.3 | 49.1 ± 9.5 * * * (p < 0.005) |
| Gra (/mL) | 350 ± 170 | 330 ± 160 | 390 ± 280 |
| Mo (/mL) | 85 ± 70 | 90 ± 100 | 120 ± 110 |
| Lym (/ mL) | 4410 ± 1590 | 4370 ± 1660 | 3210 ± 1440 * (p < 0.05) |
| CD4+ T (/mL) | 740 ± 330 | 730 ± 260 | 590 ± 280 |
| CD8+ T (/mL) | 370 ± 150 | 370 ± 140 | 340 ± 180 |
| B (/mL) | 2650 ± 1080 | 2500 ± 1020 | 1640 ± 970 ** (p < 0.01) |
| RBC (/mL) | 862 ± 68 | 867 ± 65 | 835 ± 104 |
| Hb (g/dL) | 12.6 ± 0.9 | 13.0 ± 1.1 | 11.9 ± 1.8 |
| Ht (%) | 39.1 ± 2.3 | 40.4 ± 2.8 | 36.8 ± 5.1 |
| Plt (/mL) | 42.4 ± 13.9 | 45.3 ± 12.3 | 55.8 ± 23.6 (p = 0.06) |

As shown in Table 1, Ndufs4 knockout mice displayed decrease in the number of whole blood cells. As shown in Table 1, Ndufs4 knockout mice displayed statistically significant decrease in lymphocytes and B cells.

Figure 2:
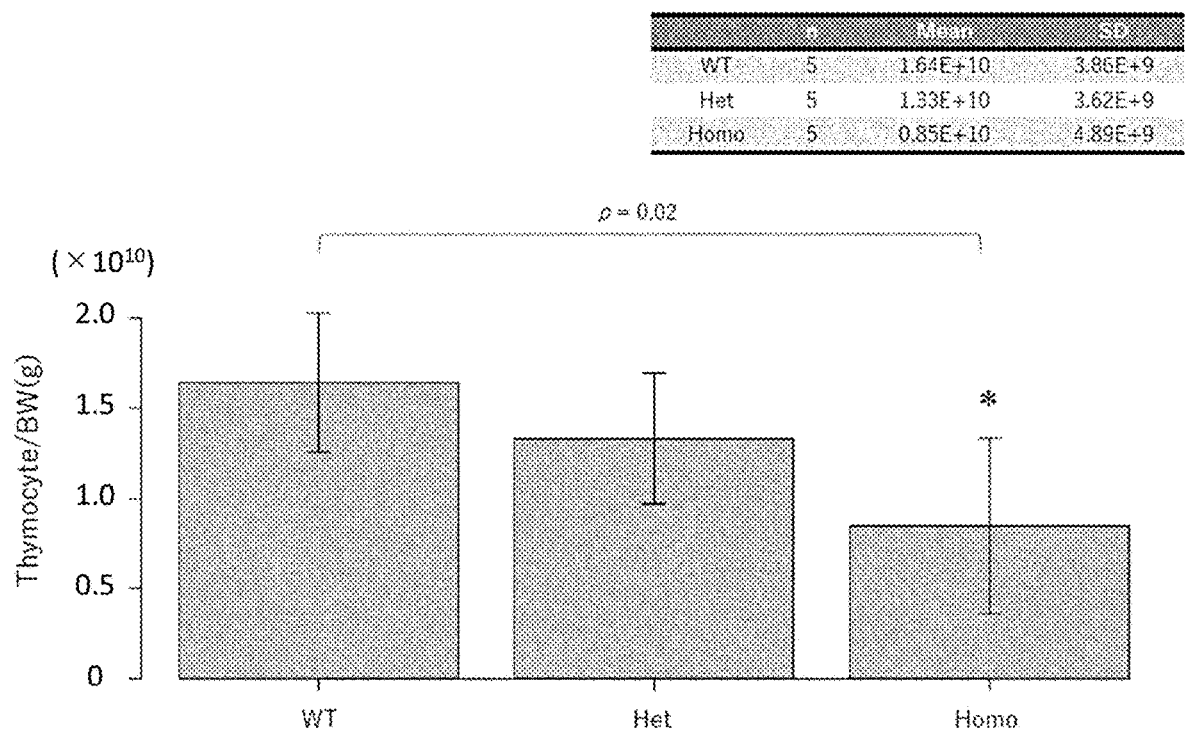
FIG. 2 shows comparison of the cell number in the thymus per body weight (BW) in wild types (WT), Ndufs4 heterozygous knockout mice (Het), and Ndufs4 homozygous knockout mice (Homo).
Figure 3:
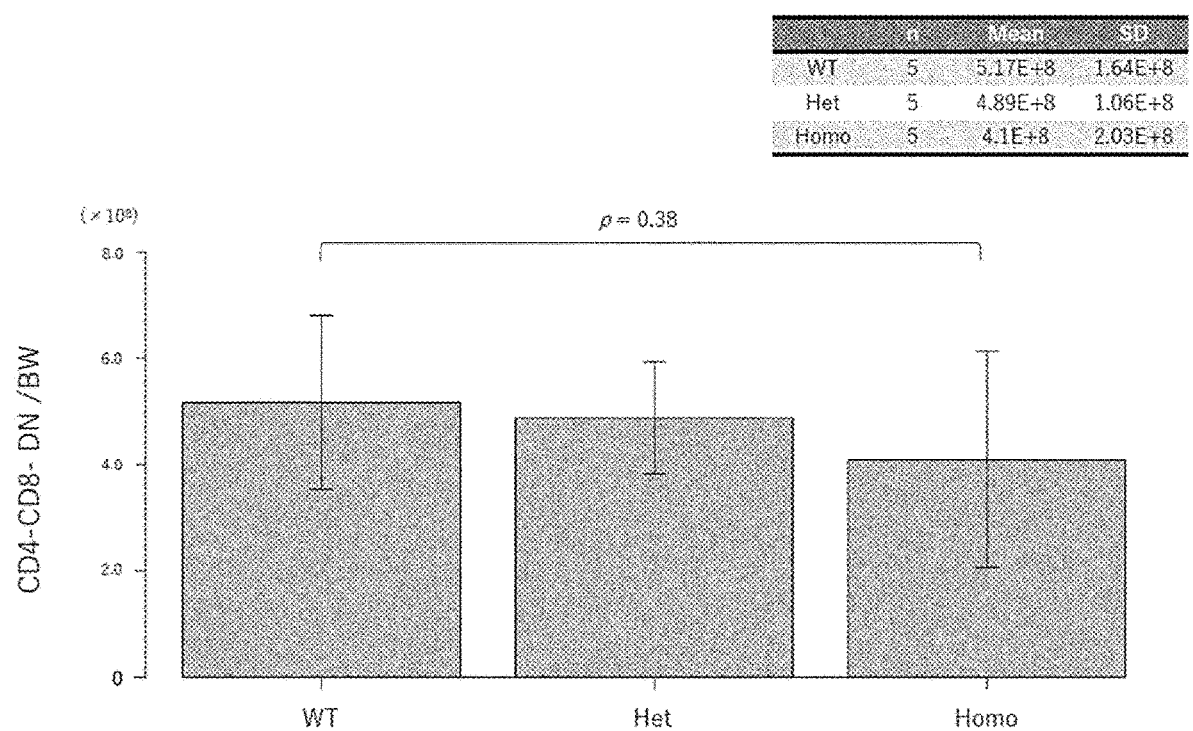
FIG. 3 shows comparison of the number of CD4/CD8 double-negative cells per body weight (BW) in wild types (WT), Ndufs4 heterozygous knockout mice (Het), and Ndufs4 homozygous knockout mice (Homo).
Figure 4:
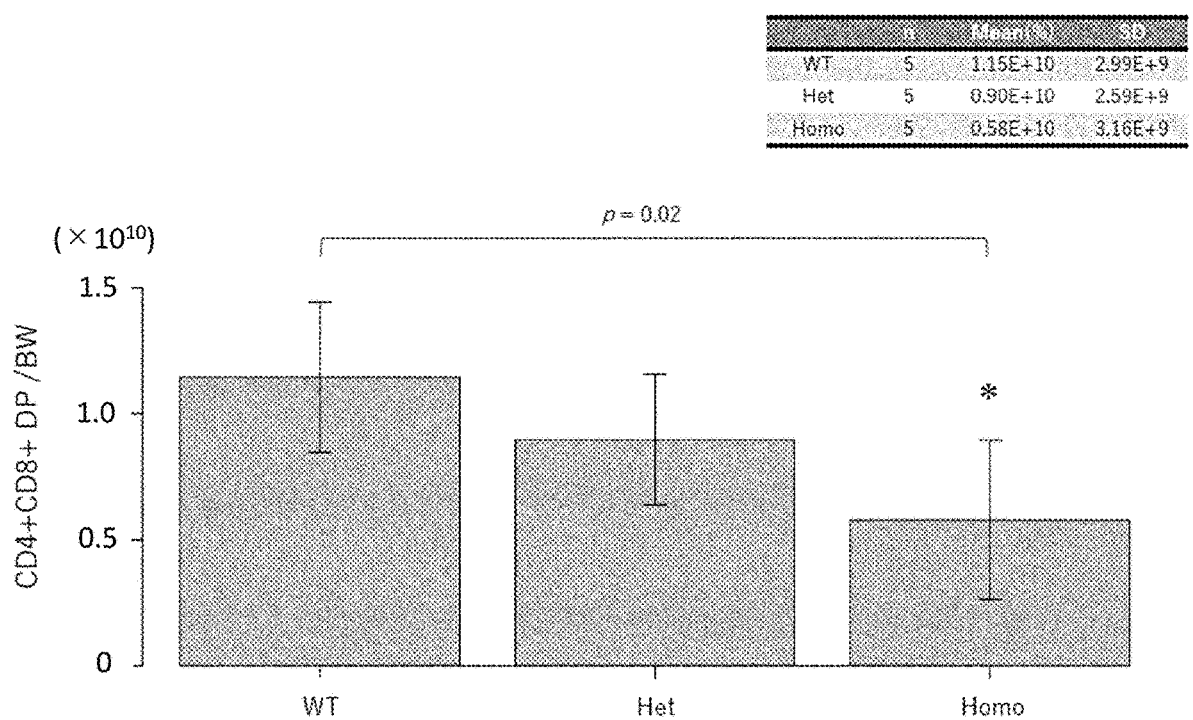
FIG. 4 shows comparison of the number of CD4/CD8 double-positive cells per body weight (BW) in wild types (WT), Ndufs4 heterozygous knockout mice (Het), and Ndufs4 homozygous knockout mice (Homo).

Thymuses were individually excised from wild types, heterozygous mice, and Ndufs4 knockout mice, and subjected to counting of the number of thymus cells in the thymuses. The results, as shown in FIG. 1, revealed that Ndufs4 homozygous knockout mice had significantly decreased number of thymus cells relative to wildtype or heterozygous mice. Moreover, as shown in FIG. 2, the number of thymus cells per body weight (BW) in Ndufs4 homozygous knockout mice was also significantly decreased relative to that in wildtype or heterozygous mice. Furthermore, the number of CD4/CD8 double-negative T cells and the number of CD4/CD8 double-positive T cells were counted from the thymus cells by flow cytometry. The results, as shown in FIG. 3, revealed that the cell number of CD4/CD8 double-negative cells per body weight had tendency to decrease in Ndufs4 knockout mice relative to wildtype or heterozygous mice. Additionally, as shown in FIG. 4, the cell number of CD4/CD8 double-positive T cells per body weight was statistically significantly decreased in Ndufs4 knockout mice relative to wildtype or heterozygous mice. As given above, Ndufs4 knockout mice had an atrophying thymus, and statistically significantly decreased in the number of thymus cells and the cell number of CD4/CD8 double-positive T cells per body weight relative to wildtype or heterozygous mice. Greater degree of decrease in the number of thymus cells and the number of CD4/CD8 double-positive T cells per body weight relative to that of CD4/CD8 double-negative T cells indicates that abnormality in mitochondrial function in the thymus is involved in T cell development in the thymus.

Figure 5:
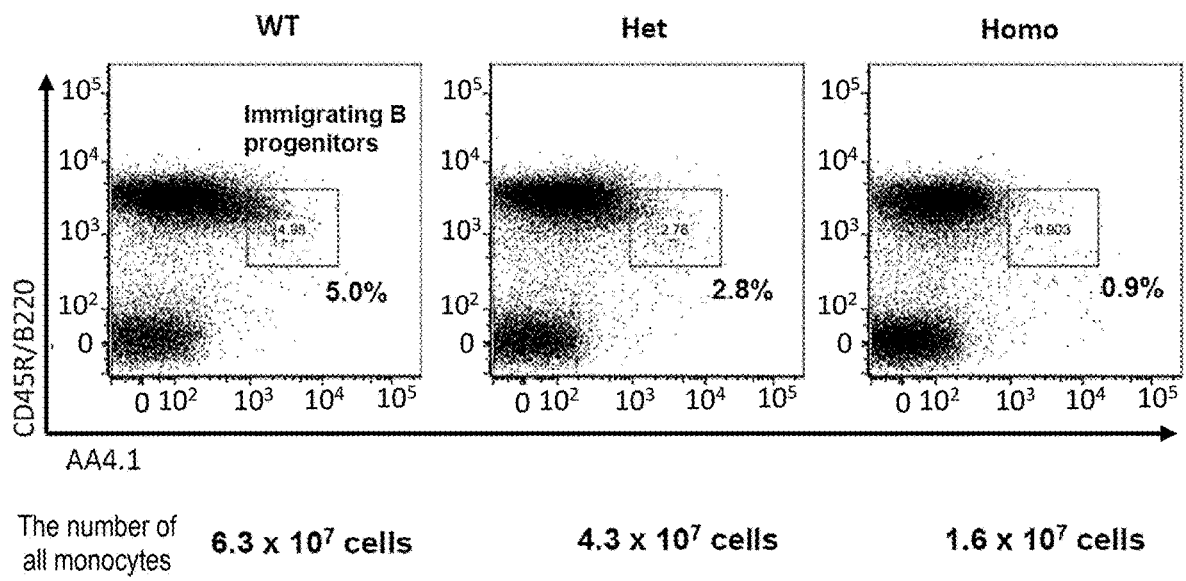
FIG. 5 shows comparison of the number of all monocytes and comparison of the ratio of progenitor cells of B cells (B cell progenitors) to all cells, in spleens of wild types (WT), Ndufs4 heterozygous knockout mice (Het), and Ndufs4 homozygous knockout mice (Homo).

Spleens were individually excised from wildtype, heterozygous, and Ndufs4 knockout mice (3-weeks old, females) obtained as littermates by mating Ndufs4 heterozygous mice to each other, and then B-cell progenitor cells gathering in the spleens were analyzed by flow cytometry based on the expressions of AA4.1, CD45R, and B220. The results, as shown in FIG. 5, revealed that Ndufs4 knockout mice had significantly reduced number of all monocytes, and also had reduced ratio of B-cell progenitor cells, relative to wildtype and heterozygous mice.

Figure 6:
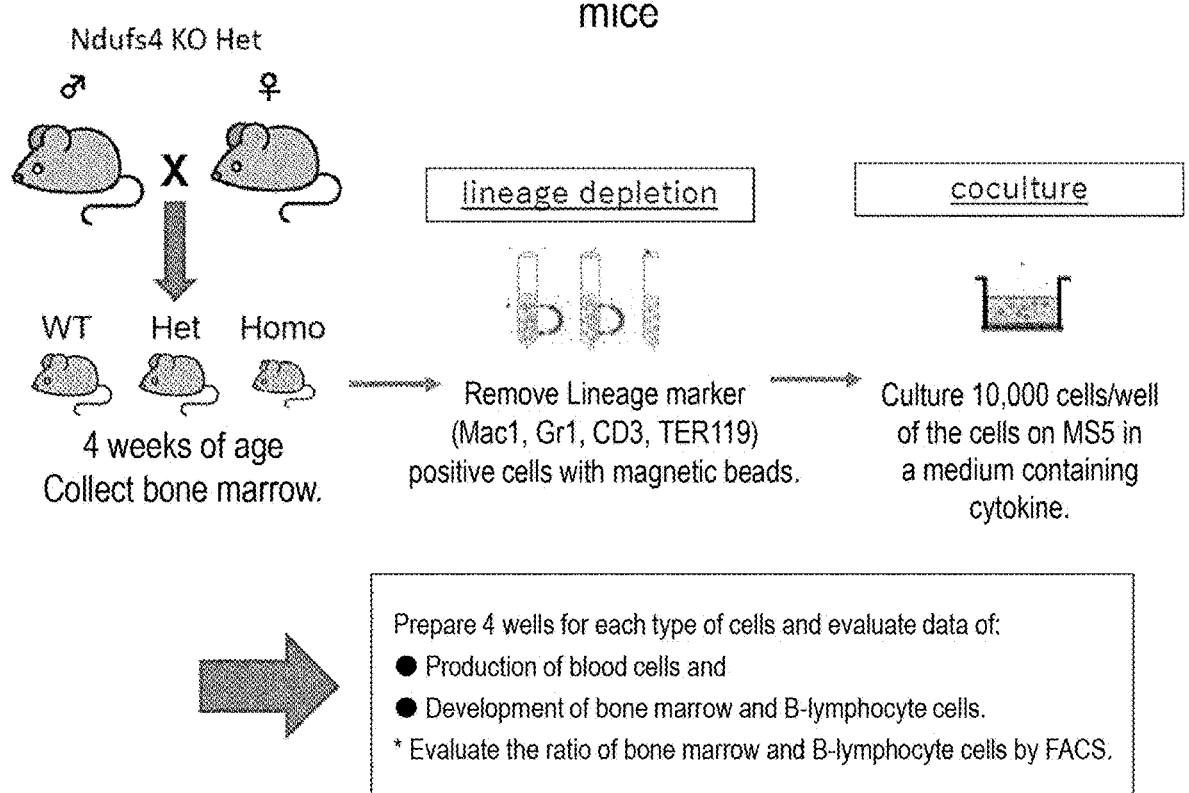
FIG. 6 shows an isolation scheme and a subsequent culture experimental scheme of hematopoietic progenitor cells in the bone marrow of wild types (WT), Ndufs4 heterozygous knockout mice (Het), and Ndufs4 homozygous knockout mice (Homo).
Figure 7:
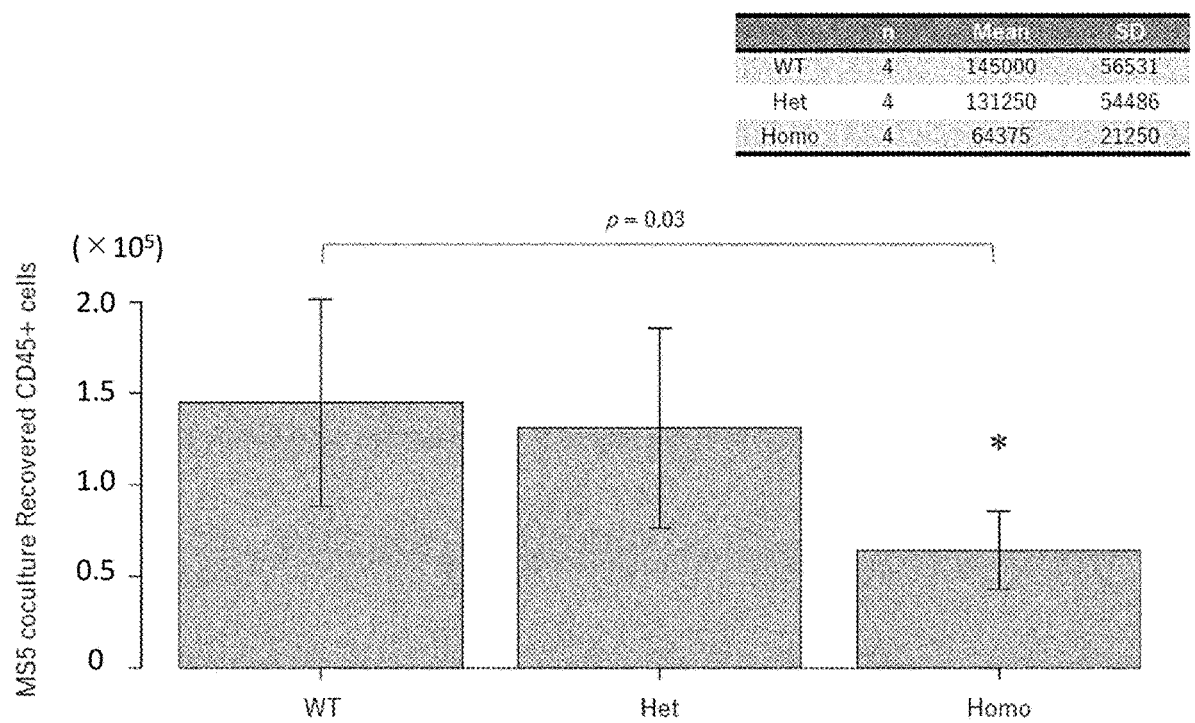
FIG. 7 shows comparison of the number of CD45-positive cells after culturing of hematopoietic progenitor cells from wild types (WT), Ndufs4 heterozygous knockout mice (Het), and Ndufs4 homozygous knockout mice (Homo).
Figure 8:
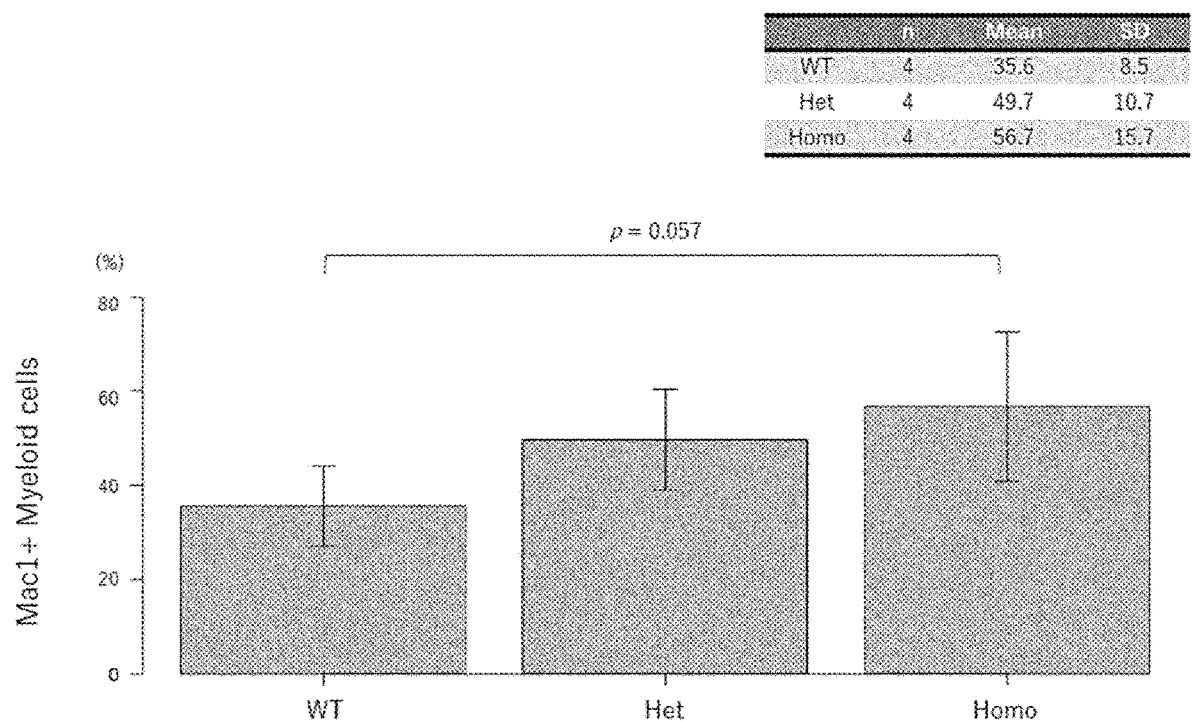
FIG. 8 shows comparison of the number of Mac1+bone marrow cells after culturing of hematopoietic progenitor cells from wild types (WT), Ndufs4 heterozygous knockout mice (Het), and Ndufs4 homozygous knockout mice (Homo).
Figure 9:
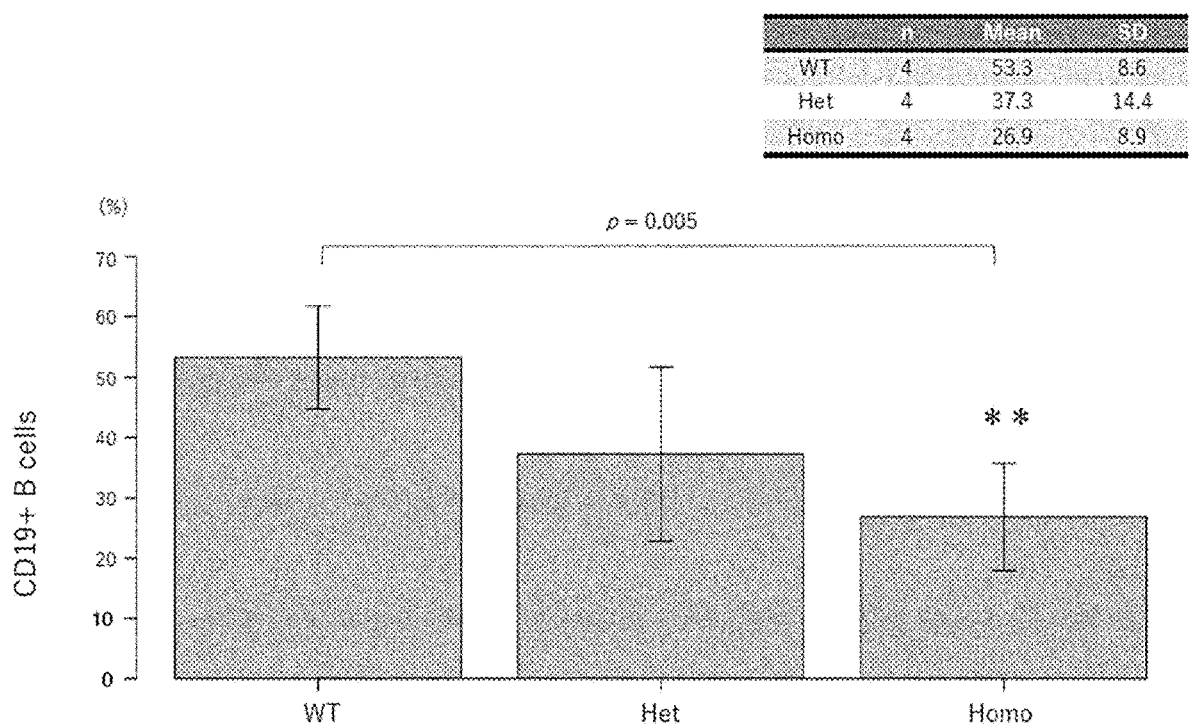
FIG. 9 shows comparison of the number of CD19-positive B cells after culturing of hematopoietic progenitor cells from wild types (WT), Ndufs4 heterozygous knockout mice (Het), and Ndufs4 homozygous knockout mice (Homo).

Hematopoietic progenitor cells were isolated from bone marrow of Ndufs4 knockout mice, and evaluated for growth and differentiation potentials. As shown in FIG. 6, bone marrow was collected from wildtype, heterozygous, and Ndufs4 knockout mice (4-week old) obtained as littermates by mating Ndufs4 heterozygous mice to each other. Using magnetic beads, lineage marker (Mac1, Gr1, B220, CD3, TER119) positive cells were removed. Then, 1×10$^4$ cells of the cells thus obtained were co-cultured with mouse MS5 stromal cells. The culture period was 1 week. The results, as shown in FIG. 7, demonstrated that the number of CD45+ cells contained in a post-culture cell population was significantly decreased in Ndufs4 knockout mice relative to wildtype and heterozygous mice. Moreover, as shown in FIG. 8, it was revealed that the ratio of Mac1+bone marrow cells contained in a post-culture cell population had tendency to increase in Ndufs4 knockout mice relative to wildtype and heterozygous mice. Furthermore, as shown in FIG. 9, the ratio of CD19+B cells was significantly decreased in Ndufs4 knockout mice relative to wildtype and heterozygous mice.

Figure 10:
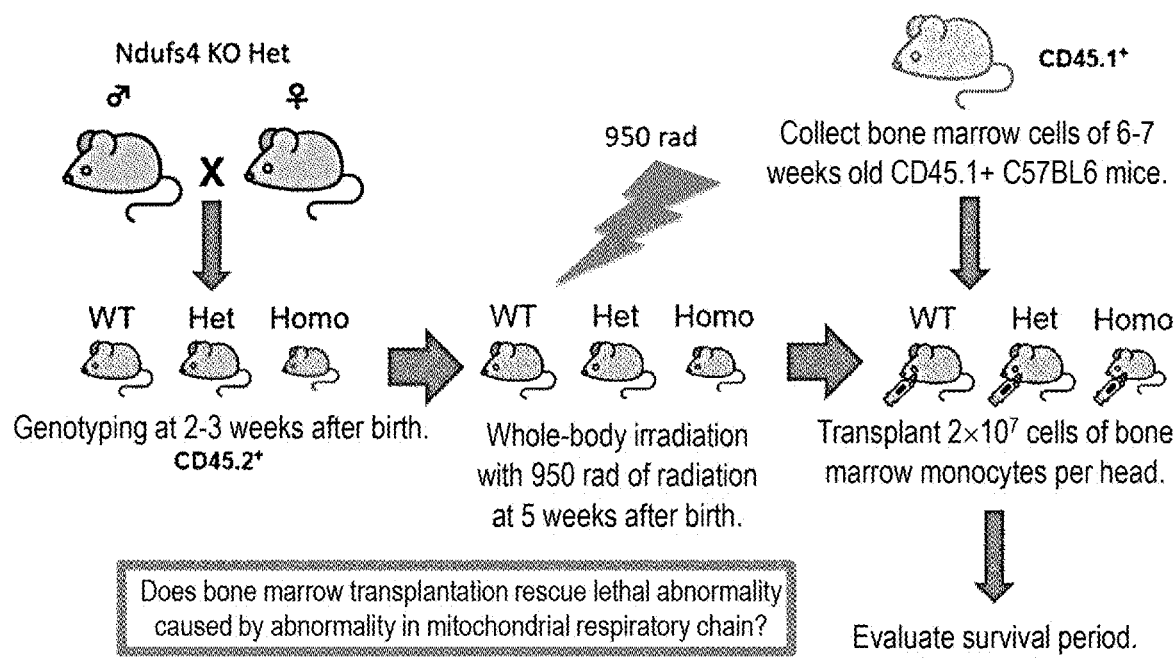
FIG. 10 show an experimental scheme of transplantation of normal bone marrow monocytes to radiated wild types (WT), Ndufs4 heterozygous knockout mice (Het), and Ndufs4 homozygous knockout mice (Homo).
Figure 11:
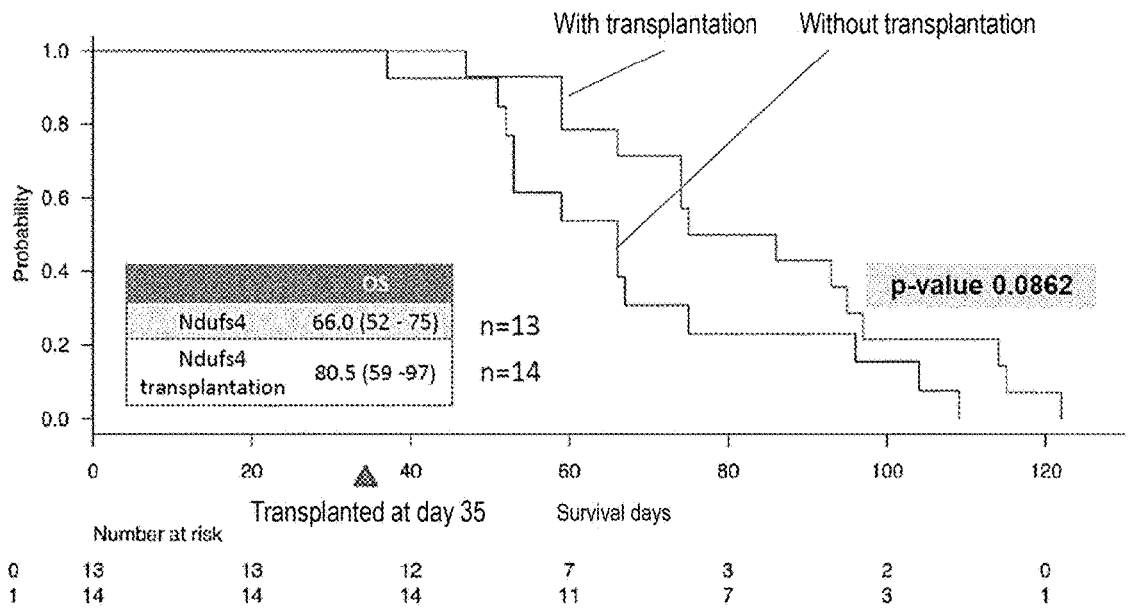
FIG. 11 shows comparison of survival curves between wildtype mice with and without bone marrow transplantation.
Figure 12:
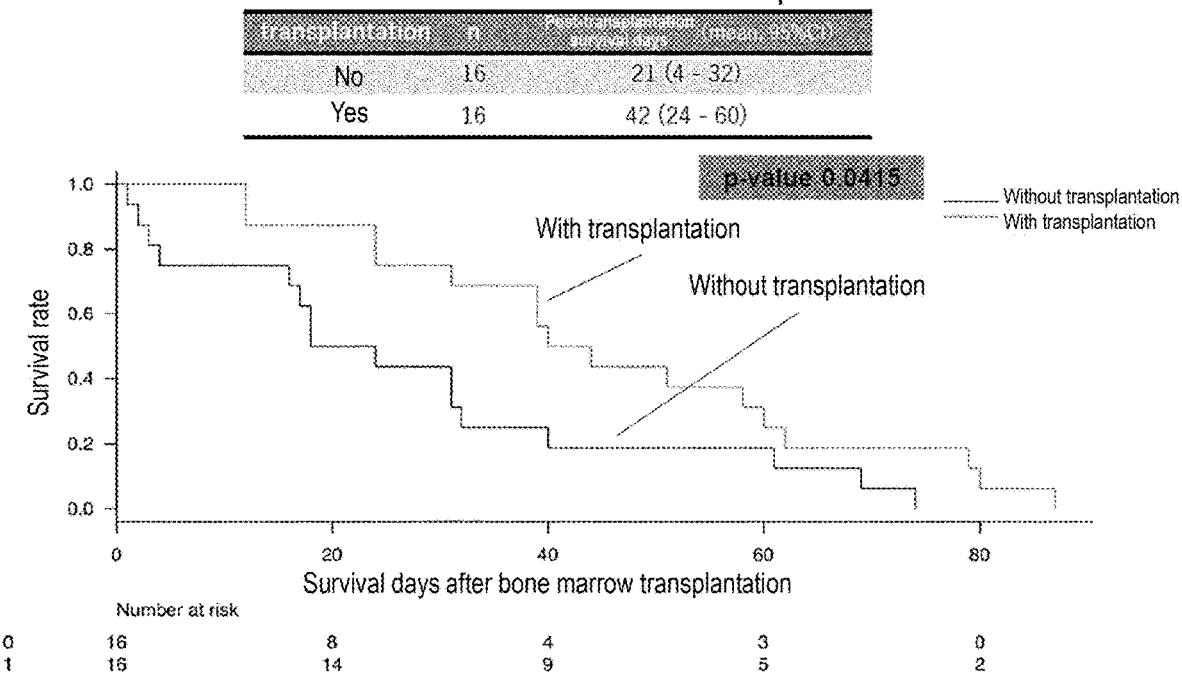
FIG. 12 shows comparison of survival curves between Ndufs4 homozygous knockout mice with and without bone marrow transplantation.
Figure 13:
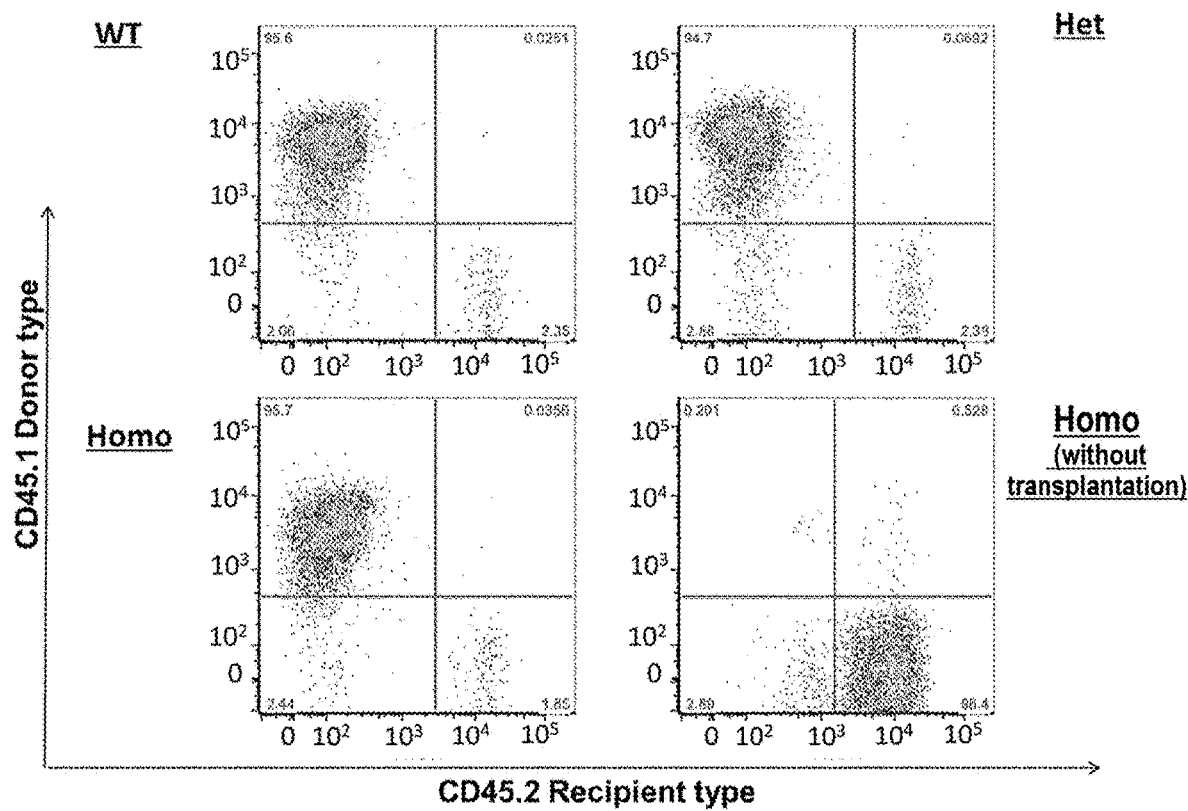
FIG. 13 shows states of survival of donor's bone marrow in wildtype mice, heterozygous knockout mice, and homozygous knockout mice after bone marrow transplantation. Also shown is survival of donor's bone marrow in homozygous knockout mice without bone marrow transplantation as a negative control.

As shown in FIG. 10, Ndufs4 knockout mice (CD45.2+) (5-weeks old) as recipients were subject to whole-body irradiation with 950 rad of radiation, administered with 2×10$^7$ cells of bone marrow monocytes from 6-7 weeks old CD45.1+ mice, and evaluated for survival period of the mice. The results, as shown in FIG. 11, demonstrate that Ndufs4 knockout mice transplanted with the bone marrow monocytes improved in overall survival (OS) relative to mice without transplantation (without radiation, without transplantation). Moreover, as shown in FIG. 12, the survival period was statistically significantly increased in Ndufs4 knockout mice transplanted with bone marrow monocytes, relative to mice without transplantation (without radiation, without transplantation). These results suggest that an abnormality of bone marrow cells occurs in Ndufs4 homozygous knockout mice. Furthermore, as shown in FIG. 13, there was no difference in engraftment of the donor cells between wildtype and heterozygous knockout mice.

Example 2: Transplantation of Healthy Mitochondria to an Ndufs4 Knockout Mouse Thymus In this Example, experiments were performed in which healthy mitochondria were transplanted to a thymus in an Ndufs4 knockout mice.

Mouse cardiac stem cells (CPCs) were used as a source of healthy mitochondria. CPCs were cultured in a DMEM-F12 medium at 37° C. for 24 hours. RES-mitochondria-directed carriers (e.g., MITO-Porters), which were produced according to the procedure disclosed in WO2018/092839, were added and incubated for 2 hours, and then RES-mitochondria-directed carriers (e.g., MITO-Porter) were introduced to CPCs. The cells thus obtained are referred to as MITO-Cells. RES-mitochondria-directed carriers (e.g., MITO-Porters) are mitochondria-directed liposomes encapsulating resveratrol, and the liposomes are liposomes composed of 1,2-dioleyl-sn-glycero-3-phosphatidylethanolamine (DOPE) and sphingomyelin (SM) at a molar ratio of 9:2, which are mitochondria-directed due to further introduction of 10% Stearyl S2 by lipid mass. WO2018/092839 shows that cells with RES-MITO-Porters introduced therein receive delivery of resveratrol into mitochondria and thus have enhanced mitochondria: e.g., though CPCs transplanted to a rat doxorubicin-induced cardiopathy model improves cell viability, MITO-Cell (referred to as MA-Cell in WO2018/092839) shows greater improvement of cell viability than CPCs.

Figure 14:
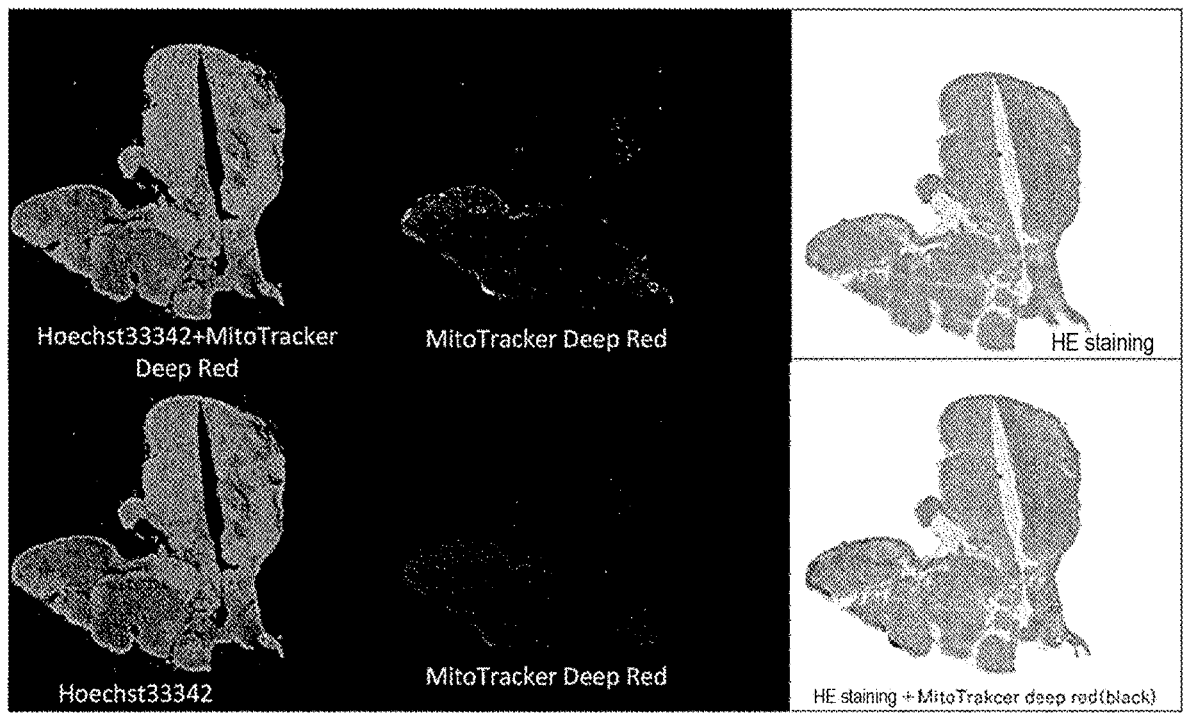
FIG. 14 shows distribution of MITO-Cell-derived mitochondria in a thymus, three days after CPCs subjected to mitochondrial activation treatment (MITO-Cell) were transplanted to the surface of the thymus.
Figure 15:
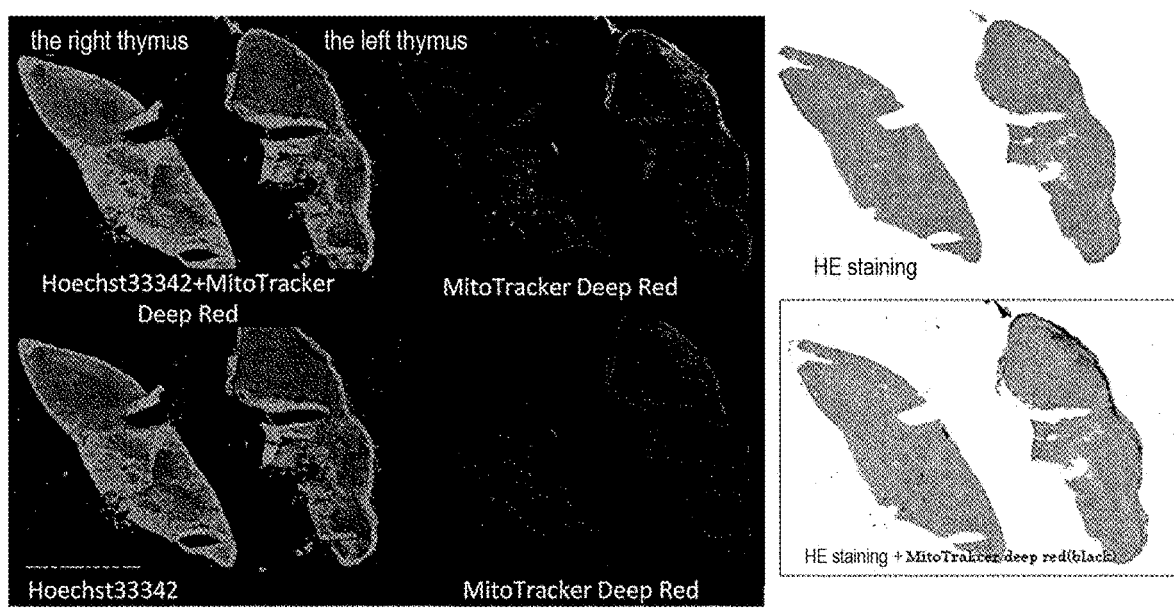
FIG. 15 shows distribution of MITO-Cell-derived mitochondria in a thymus, three days after CPCs subjected to mitochondrial activation treatment (MITO-Cell) were transplanted to the surface of the thymus.

MITO-Cells were stained with MITO Tracker deep red (manufactured by Thermo Fisher Scientific). This allowed staining of mitochondria over the MITO-Cells. After staining, the MITO-Cells ($1.0 \times 10^6$ cell) were injected to the chest-side surface of the left-side thymus (1 point) in an Ndufs4 knockout mouse. Three days after transplantation, the thymus was excised, and a tissue slice was made according to a common procedure and subjected to nuclear staining with Hoechst 33342, followed by observation with confocal laser scanning microscopy (CLMS). The results, as shown in FIGS. 14 and 15, revealed that MITO-Cell-derived mitochondria stained with MITO Tracker deep red were distributed extending beyond the administration site in the thymic tissue. This demonstrated that the mitochondria contained in the transplanted cells were widely distributed in the thymic tissue by intrathymic injection.

Example 3: Intercellular Mitochondrial Migration

This Example proves that mitochondria migrate intercellularly. For example, it is proved that mitochondria are provided from CPCs to cells of Ndufs4.

In this Example, cell populations with separately stained mitochondria are co-cultured, and after the culture, the presence or absence of bicolored cells is checked. This experiment system indicates that the bicolored cells contain mitochondria provided from two or more cells, or in other words, indicates that mitochondria migrate from a cell to another cell.

Figure 16:
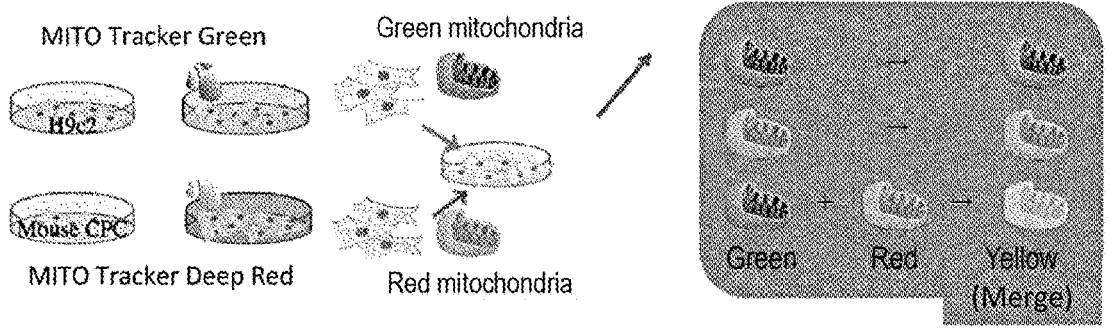
FIG. 16 illustrates an assay system for detecting intercellular mitochondrial migration.

In more particular, as shown in FIG. 16, separate staining was made for mitochondria contained in one cell population and mitochondria contained in the other cell population so as to allow for distinguish between mitochondria derived from different cells. In more particular, mitochondria in one cell population were stained with Mito tracker Green so as to emit green fluorescence, while mitochondria in the other cell population were stained with Mito tracker Deep Red so as to emit red fluorescence. Then, the two cell populations were co-cultured in a single culture liquid. In this experiment system, if mitochondria migrate intercellularly, red-stained mitochondria and green-stained mitochondria will be co-localized in a single cell, and will emit both red and green fluorescence or emit yellow fluorescence in a single cell.

Figure 17:
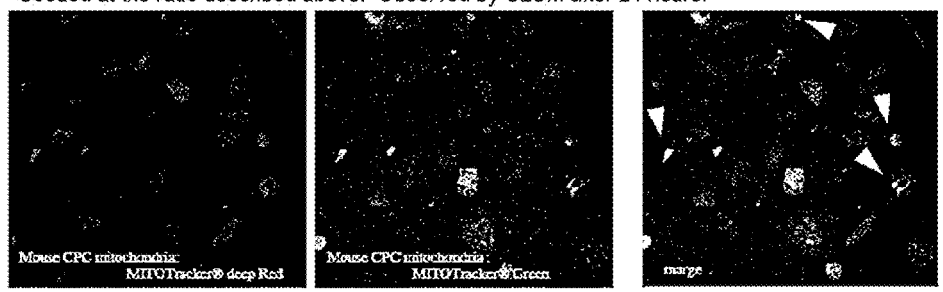
FIG. 17 represents fluorescence microscopy images of cells after 24 hours of co-culturing of mouse CPCs having mitochondria stained red and mouse CPCs having mitochondria stained green at a ratio of 1:1. The left panel represents a red image; the central panel represents a green image; and the right panel represents a merged image. In the merged image, the cells indicated with arrowheads appear yellow, thereby detecting occurrence of intercellular mitochondrial migration.
Figure 18:
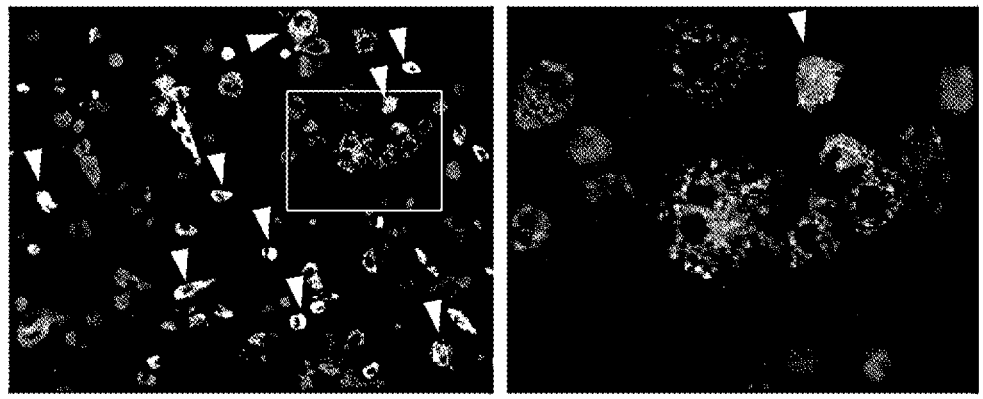
FIG. 18 represents fluorescence microscopy images of cells 24 hours after co-culturing of H9c2 cells having mitochondria stained green and CPCs having mitochondria stained red. The left panel shows a red and green merged image, in which the cells indicated with arrowheads appear yellow, thereby detecting occurrence of intercellular mitochondrial migration. The right merged image represents an enlarged view of the square region in the left image.
Figure 19:
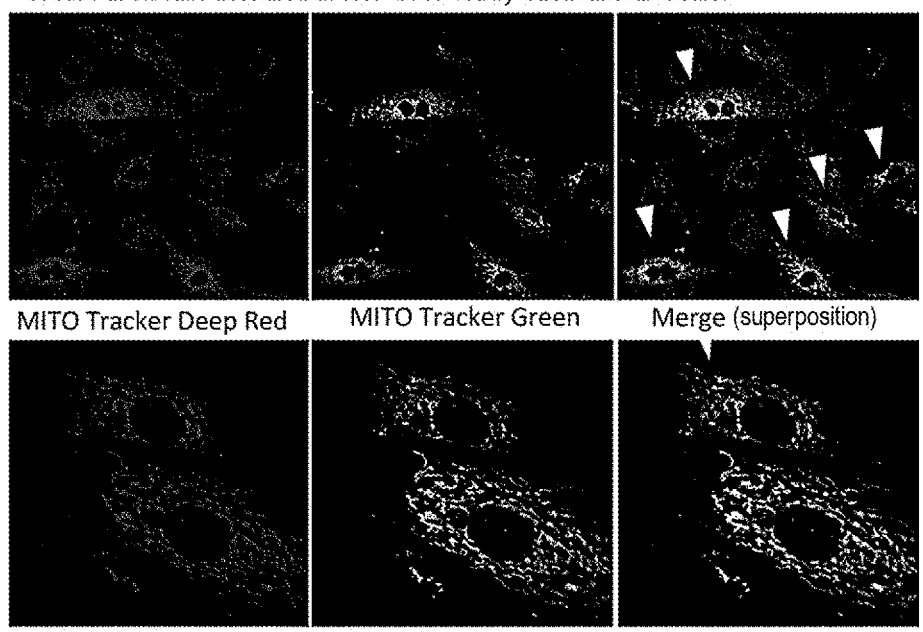
FIG. 19 represents fluorescence microscopy images of cells 24 hours after co-culturing of H9c2 cells having mitochondria stained green and CPCs having mitochondria stained red. The left panel represents a red image; the central panel represents a green image; and the right panel represents a merged image. In the merged image, the cells indicated with arrowheads appear yellow, thereby detecting occurrence of intercellular mitochondrial migration. The bottom indicates another field of view.

FIG. 17 shows observation results by CLSM 24 hours after co-culturing of mouse CPCs (red) and mouse CPCs (green). As shown in FIG. 17, some cells displayed to include cells with yellow fluorescence (see white arrowheads). This indicated that mitochondrial migration occurs between CPCs. Moreover, FIGS. 18 and 19 show observation results by CLSM 24 hours after co-culturing of H9c2 cells (green), which are rat cardiac striated muscle cells, and CPCs (red). As shown in FIGS. 18 and 19, some cells displayed to include cells with yellow fluorescence (see white arrowheads). The observation of the cells during co-culturing revealed intercellular mitochondrial migration. Additionally, the mitochondrial migration occurred from CPC to H9c2 more frequently than that from H9c2 to CPC. Furthermore, in consequence, the number of cells emitting red fluorescence was maintained, while the number of cells emitting green fluorescence decreased and the number of cells with yellow fluorescence increased. These suggest that mitochondria are likely to migrate from a stem cell to a mature cell.

Figure 20:
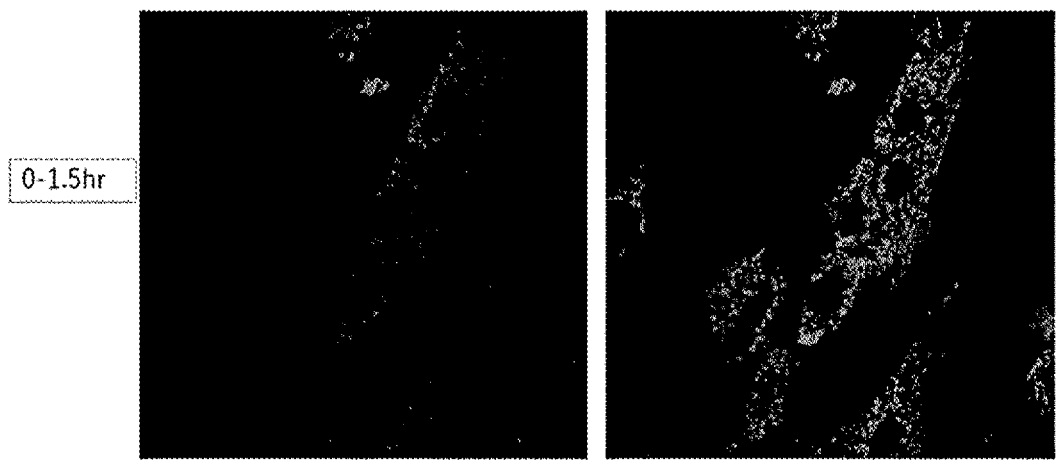
FIG. 20 shows intercellular migration of RES-MITO-Porters from MITO-Cells.
Figure 21:
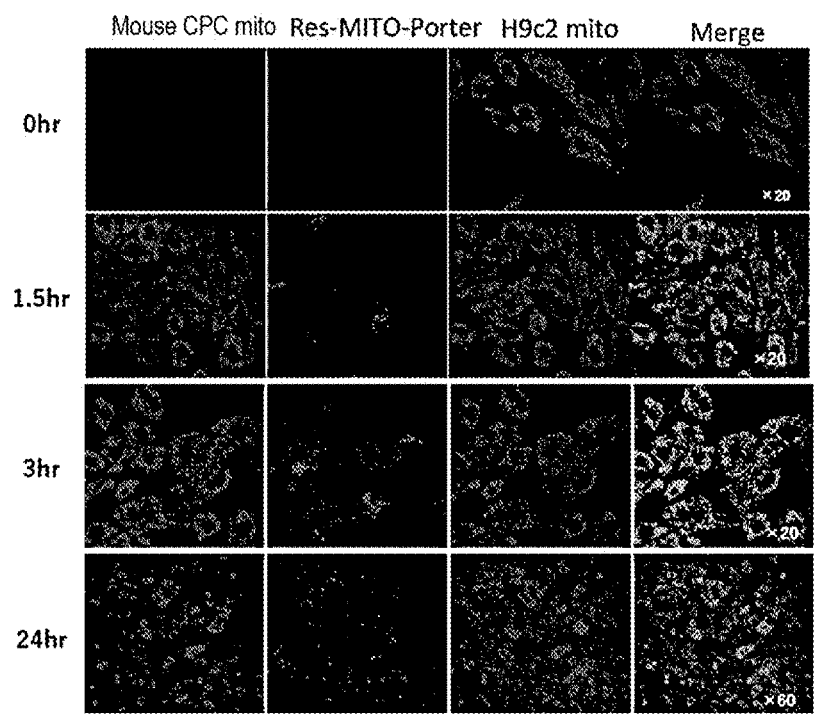
FIG. 21 shows intercellular migration of RES-MITO-Porters from MITO-Cells.

In addition, mitochondrial migration from MITO-Cells to H9c2 cells was also checked. RES-MITO-Porters were stained green with nitrobenzoxadiazole. Stained RES-MITO-Porters were used, and MITO-Cells were stained orange with MITO traker orange, and shown with blue in the Figure. Furthermore, mitochondria within H9c2 cells were stained red with MITO Tracker deep red. MITO-Cells thus obtained were recovered from a culture dish, washed and seeded in a medium, and co-cultured with H9c2 cells. At a specified time after the beginning of co-culturing, the cells were observed using CLMS. As such, intercellular migration of RES-MITO-Porters from the inside of MITO-Cells was observed. The results were as shown in FIGS. 20 and 21. As shown in FIGS. 20 and 21, it was observed that RES-MITO-Porters began to migrate intercellularly after 1.5 hours, and widely propagated over the cells after 3 hours and after 24 hours.

Figure 22:
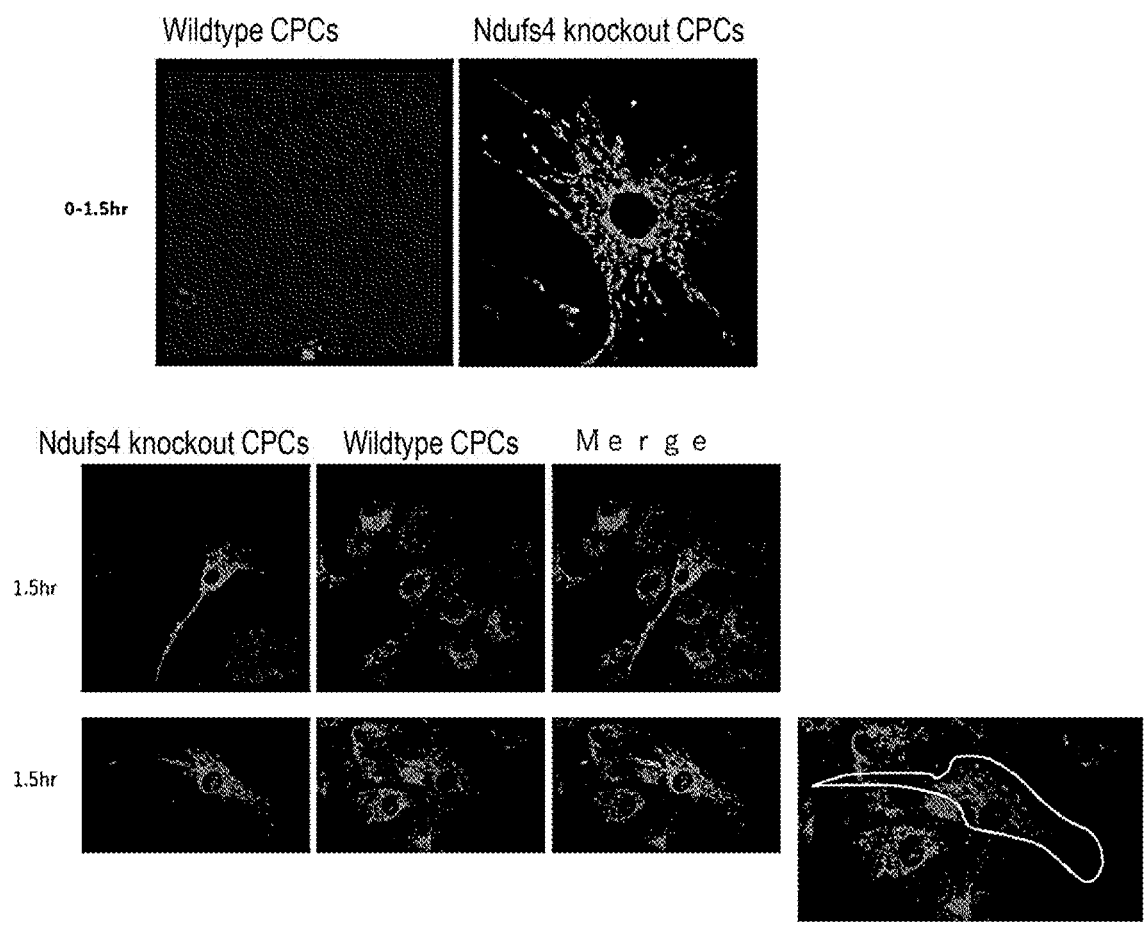
FIG. 22 shows mitochondrial migration from wildtype CPCs to CPCs of an Ndufs4 homozygous knockout mouse.

CPCs isolated from an Ndufs4 knockout mouse (green) and CPCs isolated from a wildtype mouse (red) were co-cultured and observed for intercellular mitochondrial migration. Then, as shown in FIG. 22, mitochondria emitting red fluorescence were confirmed to be present in cytoplasm of CPCs isolated from an Ndufs4 knockout mouse (see the most right-bottom panel). These results show that mitochondria migrated from wildtype mouse CPCs to Ndufs4 knockout mouse CPCs.

Ndufs4 knockout mice represent knockout with a gene encoding 18 kDa of an accessory subunit of mitochondrial respiratory chain complex I, and have abnormality in mitochondrial function. Phenotype of Ndufs4 knockout mice can be seen particularly strongly in immune cells, and had more atrophying thymus than that of wild types. Such abnormality is not an abnormality found only in Ndufs4 knockout mice, but is an abnormality also commonly found in model animals with abnormality in other mitochondrial functions (Pint M, et al., Cell Death & Differ., 2017, 24 (2): 288-99) and Dai Y, et al., Mitochondrion., 2013, 13 (4): 282-291). Abnormality in mitochondrial function has been known to also occur due to aging (Zhang R, et al., BMC Genomics, 2017, 18 (1): 890), but aging has also been known to cause thymic atrophy. In particular, the thymus reaches a peak in size around teenage, then rapidly atrophies and almost disappears by 70 years of age (Lynch H E et al., Trends Immunol., 2009, 30 (7): 366-73). Thymic atrophy can occur due to overproduction of active oxygen (Griffith A V et al., Cell Rep., 2015, 12 (7): 1071-9) in thymic interstitial cells, which are highly mitochondria-dependent cells (Doulias P T et al., Sci Signal, 2013, 6 (256): rs1). Additionally, immune abnormality has also been known to occur in thymic atrophy caused by aging (Taub D D and Longo D L, Immunol Rev., 2005, 205:72-93). Thus, there is a relationship of abnormality in mitochondrial function with thymic abnormality and immune system abnormality.

Moreover, a report says that thymic atrophy and abnormality in thymic lymphocyte improve in tail vein administration with mesenchymal stem cells (MSCs) (Jung W S et al., Cell Biol Int., 2014, 38 (10): 1106-17). Meanwhile, another report says that culture liquid of MSCs with impairment of mitochondrial respiratory chain complex I function mediate mitochondrial migration caused by extracellular granules, but does not display improvement of thymic atrophy and abnormality in thymic lymphocyte (Morrison T et al., Am J Respir Crit Care Med., 2017, 196 (10): 1275-1286).

Upon administrating wildtype CPCs to a thymus in an Ndufs4 knockout mouse, healthy mitochondria contained in the wildtype CPCs were widely distributed in the thymic tissues. The culture experiment revealed that mitochondria can migrate intercellularly, and particularly had an ability of migrating from wildtype cells to Ndufs4 knockout mouse cells. Moreover, the mitochondria were not always localized within the cells, and frequently migrated intercellularly. This can be interpreted that, according to the present invention, transplantation of mitochondria having healthy respiratory chain complexes to the thymus allows the mitochondria to be widely distributed over the thymus. These experimental results showed that mitochondria having healthy respiratory chain complexes are transplanted to a tissue having reduced mitochondrial function, thereby allowing the mitochondria having healthy respiratory chain complexes to be widely distributed throughout the tissue. Thus, the present invention provides a technique for locally injecting mitochondria having healthy respiratory chain complexes to the thymus of an individual having abnormality in mitochondrial function, thereby providing the mitochondria having healthy respiratory chain complexes to the thymus.

Restoration of mitochondrial function in the thymus is considered to induce restoration of decreased thymic function, improvement of thymic atrophy, and improvement of immune abnormality. Therefore, the thymus provided with mitochondria having healthy respiratory chain complexes is considered to be rescued from its decreased function or functional abnormality, and the present invention can be useful in treating an individual having an abnormality in mitochondrial function (e.g., a mitochondrial disease patient or a 60 or more years old individual).

In particular, a thymus provided with activated mitochondria is considered to be more strongly rescued from its decreased function or functional abnormality (WO2018/092839). Accordingly, the present invention provides a technique for providing the thymus with activated mitochondria, and may be useful in treating an individual having abnormality in mitochondrial function (e.g., a mitochondrial disease patient or a 60 or more years old individual).

What is claimed is:

1. A method, comprising: intra-thymically administering to a subject in need thereof a pharmaceutical formulation comprising mitochondria encapsulated within cells, wherein the cells are selected from the group consisting of a cardiac stem cell and a cardiac progenitor cell,
   wherein the cells have been treated with a mitochondrial activator prior to the intra-thymical administration,
   whereby the cells transfer their mitochondria to mature cells originally present in the thymic tissue.

2. The method of claim 1, wherein the subject has an abnormality in mitochondrial function.

3. The method of claim 1, wherein the subject has an abnormality in mitochondrial function, wherein the subject further has an abnormality in immune function, and wherein the abnormalities are therapeutically treated by the method.

4. The method of claim 1, wherein the subject has an abnormality in mitochondrial function, wherein the subject further has thymic atrophy, and wherein the thymic atrophy is alleviated by the method, thereby leading to functional recovery of autoimmune T cells.

5. A method, comprising: intra-thymically administrating to a subject in need thereof a pharmaceutical composition comprising intact mitochondria isolated from cells selected from the group consisting of a cardiac stem cell and a cardiac progenitor cell,
   wherein the cells have been treated with a mitochondrial activator prior to mitochondrial isolation,
   whereby the mitochondria are transferred to mature cells originally in thymic tissue.

6. The method of claim 5, wherein the intact mitochondria have been isolated from cells with enhanced permeability by digitonin treatment.

* * * * *